United States Patent [19]

Suzuki et al.

[11] Patent Number: 5,016,688
[45] Date of Patent: May 21, 1991

[54] ROLLER BOTTLE FILLING AND HARVESTING SYSTEM

[75] Inventors: Akira Suzuki; Shoichi Matsuda, both of Tokyo; Yasutami Muto, Akayama; Kazuo Aoki, Tokyo, all of Japan

[73] Assignee: Kirin Beer Kabushiki Kaisha, Tokyo, Japan

[21] Appl. No.: 417,645

[22] Filed: Oct. 5, 1989

[30] Foreign Application Priority Data

| Oct. 7, 1988 | [JP] | Japan | 63-253553 |
| Oct. 7, 1988 | [JP] | Japan | 63-253554 |
| Oct. 7, 1988 | [JP] | Japan | 63-253555 |
| Oct. 18, 1988 | [JP] | Japan | 63-262069 |
| Oct. 18, 1988 | [JP] | Japan | 63-262070 |

[51] Int. Cl.⁵ ............................................. B65B 31/02
[52] U.S. Cl. ...................................... 141/170; 141/92; 141/129; 141/165; 53/167; 53/425; 53/468; 53/510
[58] Field of Search ............... 141/129, 164, 165, 168, 141/169, 170, 171, 172, 89, 90, 91, 92, 85; 53/510, 167, 282, 425, 468

[56] References Cited

U.S. PATENT DOCUMENTS

| 2,614,740 | 10/1952 | Moser | 141/165 |
| 3,190,321 | 6/1965 | Robinson | 141/92 |
| 4,349,053 | 9/1982 | Eisenberg | 141/171 |
| 4,456,040 | 6/1984 | Bacroix et al. | 141/171 |
| 4,494,583 | 1/1985 | Reeves, Jr. et al. | 141/168 |
| 4,761,936 | 8/1988 | Suzuki et al. | 53/167 |
| 4,913,179 | 4/1990 | Engel et al. | 141/91 |

FOREIGN PATENT DOCUMENTS

| 564583 | 2/1958 | Belgium | 141/89 |
| 1906266 | 5/1970 | Fed. Rep. of Germany | 141/171 |
| 407672 | 3/1934 | United Kingdom | 141/85 |

Primary Examiner—Henry J. Recla
Assistant Examiner—Casey Jacyna
Attorney, Agent, or Firm—Ladas & Parry

[57] ABSTRACT

In the roller bottle filling and harvesting system of the present invention, a decapper, a medium harvesting and cleaning apparatus, a medium filling apparatus and a capper are all located in an aseptic chamber, in this order along a supply conveyor. Roller bottles at the medium harvesting and cleaning apparatus have their pitch aligned and a plural number of roller bottles are tilted from the upright position, through a predetermined angle and the used medium in the roller bottles is withdrawn, the bottles returned to the upright position and then filled with cleaning liquid by a roller bottle inner surface cleaning apparatus. Then, the roller bottles are sent to a roller bottle roll and tilt apparatus which tilts the roller bottles to a predetermined angle and rotates and cleans the roller bottles and then sends them to an adjacent supply conveyor. Furthermore, the plural number of roller bottles aligned and supplied to the medium filling apparatus, are tilted through a predetermined angle and the cleaning liquid inside them is withdrawn. The bottles are then returned to the upright position, filled with the required amounts of medium and $CO_2$ gas by a double nozzle for the simultaneous filling thereof, in order to adjust the pH value, and are then sent to an adjacent supply conveyor.

8 Claims, 16 Drawing Sheets

ROLLER BOTTLE FILLING AND HARVESTING SYSTEM

BACKGROUND OF THE INVENTION

The present invention relates to a roller bottle filling and harvesting system for processes for the culture of adhesive cells such as animal cells, plant cells and microbes of the adhesive type, and that can perform the processes of filling cell culture containers of the roller bottle type (hereinafter termed "roller bottles") with serum medium or the like, cleaning and exchanging the medium, and cell inoculation, and the accompanying processes of roller bottle decapping and capping automatically and at high-speed under aseptic conditions.

Conventionally, free culture containers using hollow fibers or micro-carriers have been used as culture containers for adhesive cells such as animal cells. However, it is not possible to cultivate certain types of cells except for roller bottles. Culture in roller bottles had not been automated or mechanized and so the work for filling the roller bottles with medium and the cell inoculation and other tasks had to be performed manually. And furthermore, the roller bottles for the processing general have a small capacity of about 2,000 to 3,000 ml.

Because of this, many persons had to be used when the culture of large volumes of adhesive-type animal cells was performed using roller bottles. This means, therefore, the incidence of microbial contamination caused by workers are high.

Furthermore, the use of playback-type robots to fully automize roller bottle cell culture without intervention by humans and under aseptic conditions therefore had been proposed. However, this resulted not only in the necessity to have an equal number of playback-type robots as there were humans in the first place, but also other problems such as the processing devices becoming large and complex, and difficulties in controlling the robots.

Also, widely used is a conventional type of roller bottle filling and harvesting system as shown in FIG. 20 for U.S. Pat. No. 4761936. As is disclosed in this patent, cells, particularly animal cells, are cultivated in roller bottles B which are handled or processed by a system comprising a decapper 604, the first liquid withdrawing and filling machine 605 in which culture medium is withdrawn and a bottle cleaning liquid is supplied, a bottle rolling mechanism 617 for washing the inner wall of the bottle in a horizontally-reclined state while rolling the same, the second liquid withdrawing and filling machine 605a in which the cleaning liquid is withdrawn and culture medium is supplied, and a capper 627. The decapper, the first liquid withdrawing and filling machine, the bottle rolling mechanism, the second liquid withdrawing and filling machine, and the capper are all located in an aseptic chamber 603, in this order along a conveyor 602 which extends between a bottle supply turntable 601 and a bottle collecting turntable 628.

In this type of conventional roller bottle filling and harvesting system, much space is required for installation because the weight of the roller bottles is used to make them fall and tilt within a specific space in which the roller bottle is then cleaned. This requires much space for installation and moreover, because the weight of the bottles is used to make the bottles tilt from the upright position, it is very difficult to achieve high-speed and automated cleaning processing as there is a clear limit to the processing performance.

In view of these problems, the present invention has as an objective the provision of a roller bottle filling and harvesting system of a relatively simple structure, using a mechanism to forcedly tilt the roller bottles, and perform the processes of filling cell culture containers of the roller bottle type with cell culture medium, cleaning and exchanging the medium, and cell inoculation, and the accompanying processes of roller bottle decapping and capping automatically at high-speed under aseptic conditions and without the use of manual processes or the use of playback type robots.

SUMMARY OF THE INVENTION

In order to attain the objectives described above, the roller bottle filling and harvesting system of the present invention, a decapper, a medium harvesting and cleaning apparatus, a medium filling apparatus and a capper are all located in an aseptic chamber, in this order along a supply conveyor. Roller bottles at the medium harvesting and cleaning apparatus have their pitch aligned and a plural number of roller bottles are tilted from the upright position, through a predetermined angle and the used medium in the roller bottles is withdrawn, the bottles returned to the upright position and then filled with cleaning liquid by a roller bottle inner surface cleaning apparatus. Then, the roller bottles are sent to a roller bottle roll and tilt apparatus which tilts the roller bottles to a predetermined angle and rotates and cleans the roller bottles and then sends them to an adjacent supply conveyor. Furthermore, the plural number of roller bottles that have had their pitch aligned and that have been supplied to the medium filling apparatus, are tilted through a predetermined angle and the cleaning liquid inside them is withdrawn. The bottles are then returned to the upright position, filled with the required amounts of medium and $CO_2$ gas by a double nozzle for the simultaneous filling of medium and $CO_2$ gas, and are then sent to an adjacent supply conveyor.

In roller bottle filling and harvesting system having the configuration as described above, a line of roller bottles is supplied from the roller bottle supply turntable to the supply conveyor. The roller bottles are first decapped by a decapper and their pitch is then aligned by a pitch alignment worm and a plural number of roller bottles is sent at once by the roller bottle feeder to the medium harvesting and cleaning apparatus where they are tilted to a predetermined angle and the used medium in the roller bottles is withdrawn and removed. The roller bottles for which the used medium has been withdrawn and removed are then returned to the upright position once again and cleaning liquid is introduced into them by the roller bottle inner surface cleaning apparatus. The bottles are then tilted through a predetermined angle and rotated and cleaned for the required time by the roller bottle tilt and roll apparatus, and are then returned to the adjacent supply conveyor. In addition, the upright bottles sent by the supply conveyor have their pitch aligned by the pitch alignment worm once again and are sent to the medium filling apparatus. At the medium filling apparatus, a plural number of roller bottles are tilted through a predetermined angle, the cleaning liquid inside the roller bottles is withdrawn, are returned to the upright position and are filled with predetermined amounts of medium and $CO_2$ gas by the double nozzle for the simultaneous filling of medium and $CO_2$ gas, and are then sent to the adjacent supply conveyor which sends the roller bottles to a capper which caps them. The bottles are then sent from the aseptic chamber to the culture where the culture of the necessary cells can take place.

DETAILED DESCRIPTION OF THE PREFERRED EMBODIMENTS

Roller bottle filling and harvesting system

Figure 1:
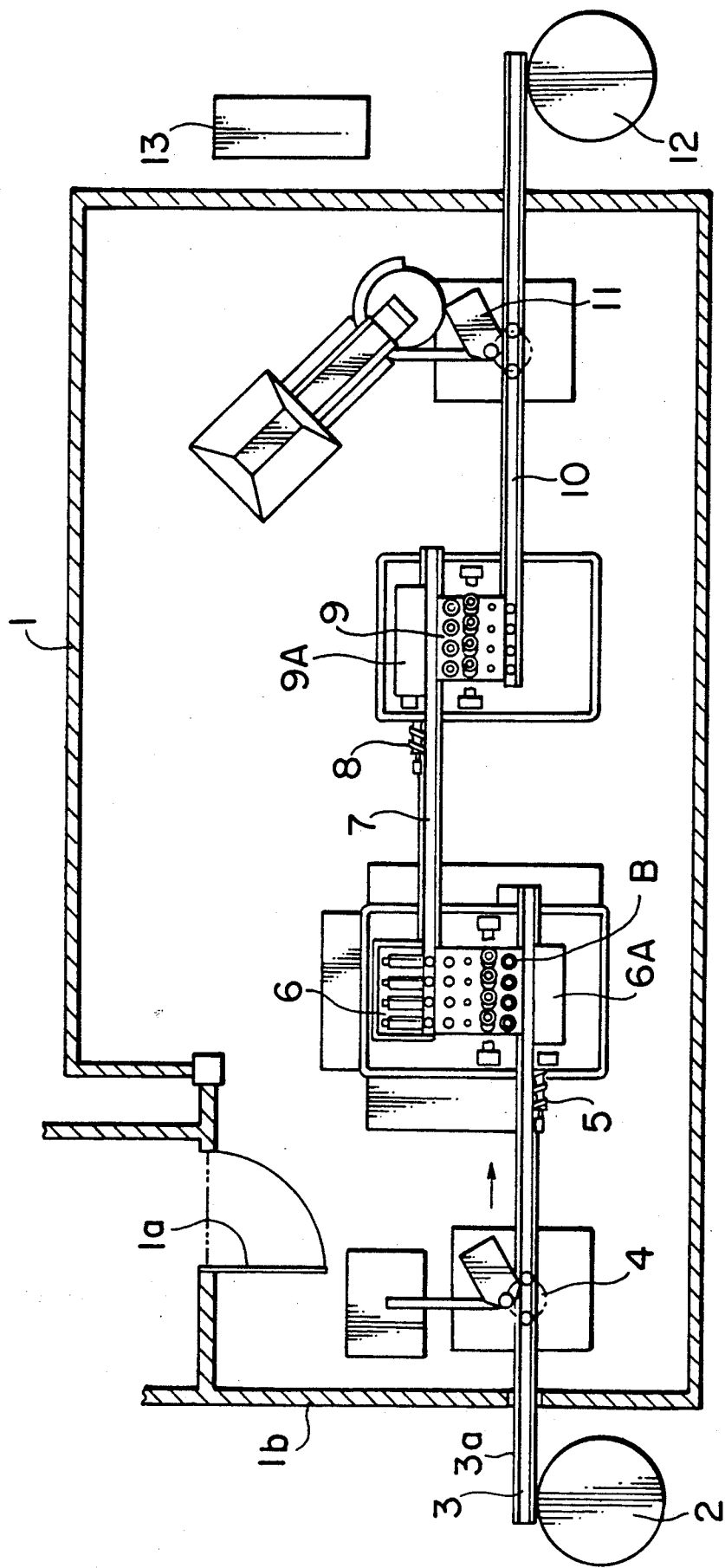
FIG. 1 is a plan view of the roller bottle filling and harvesting system according to the present invention.
Figure 2:
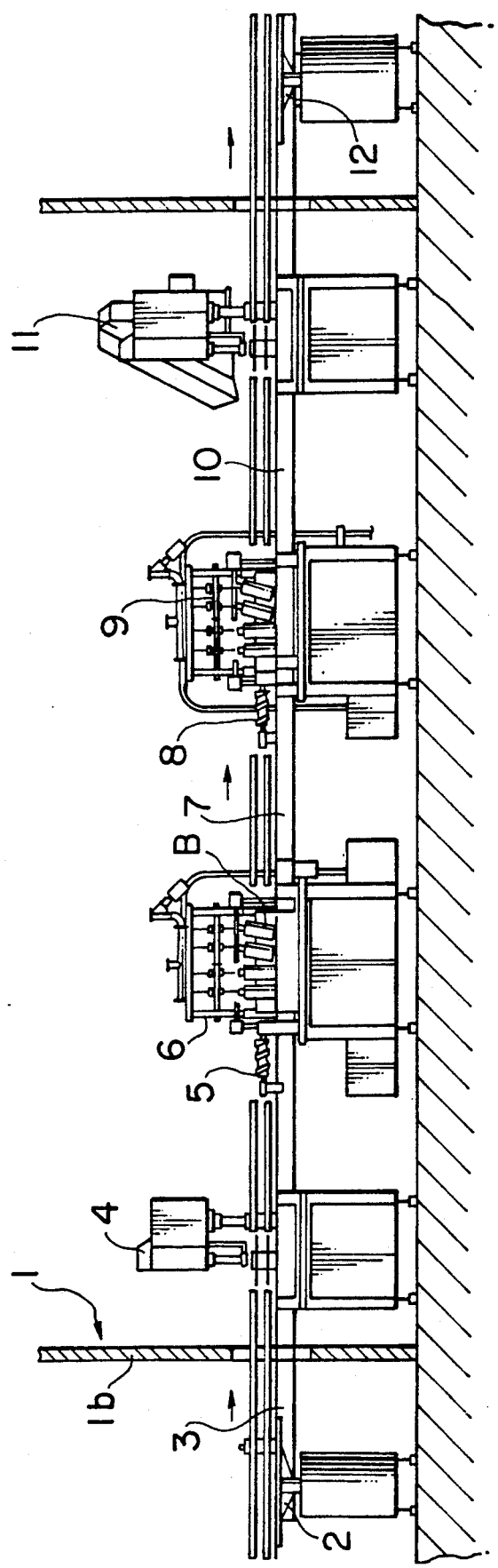
FIG. 2 is a front elevational view of the roller bottle filling and harvesting system according to the present invention.

The drawings illustrate one embodiment of a roller bottle filling and harvesting system according to the present invention. As is shown in FIG. 1, the roller bottle filling and harvesting system according to the present invention has its major parts housed in an aseptic chamber 1 surrounded by walls 1b, with access to the system being possible by a door 1a. The system is provided in the order of processing, with a roller bottle supply table 2, a first supply conveyor 3, a decapper 4, a medium harvesting and cleaning apparatus 6, a second supply conveyor 7, a medium filling apparatus 9, a third supply conveyor 10, a capper 11 and a roller bottle turntable 12. Moreover, in this embodiment of the present invention, the series of apparatus comprising the system are disposed in a straight line in the socalled "I-line" arrangement but it is also possible to have a "U-line" arrangement because of spatial limitations imposed by the aseptic chamber.

Figure 3:
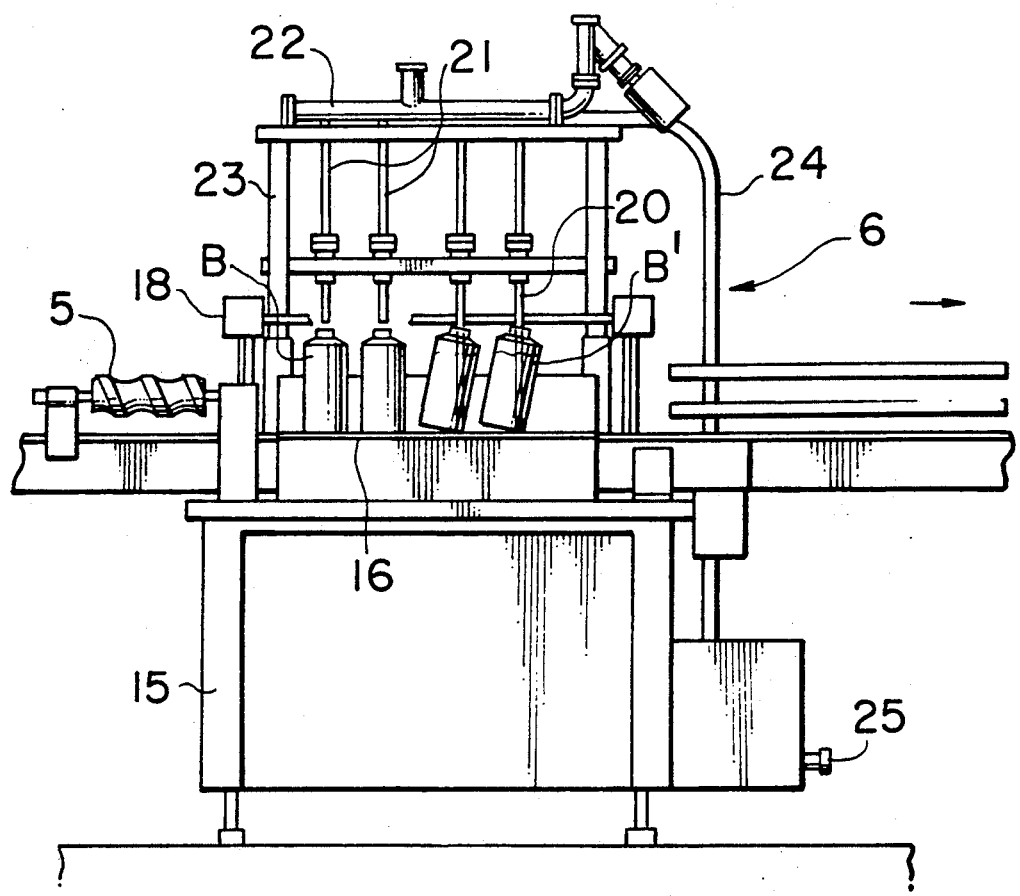
FIG. 3 is a front elevational view of the medium harvesting and cleaning apparatus according to the present invention.
Figure 4:
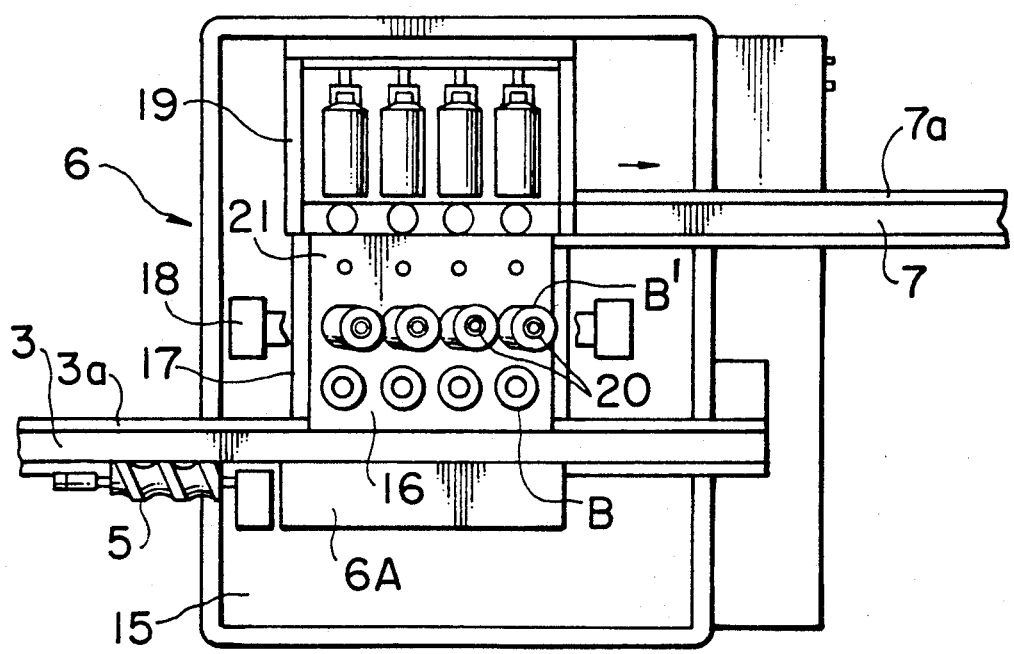
FIG. 4 is a plan view of the medium harvesting and cleaning apparatus according to the present invention.

In such a configuration as this, roller bottles B in which the culture of adhesive animal cells is performed, are rotated by the roller bottle supply table 2 and supplied in the upright state to the first supply conveyor 3. Furthermore, the roller bottle supply table 2 rotates at the same speed as the first supply conveyor 3. The first supply conveyor 3 conveys the roller bottles B into the aseptic chamber 1 through the wall 1b of the aseptic chamber 1, and the roller bottles B on the first supply conveyor 3 are decapped by a decapper 4 provided in the aseptic chamber 1. A cap sensor detects whether a roller bottle B has a cap or not. Then, the roller bottles B are conveyed by first supply conveyor 3 in the direction of the arrow as shown in FIG. 1, and while the roller bottles B are being conveyed, the pitch of a predetermined number (for example, four) of the roller bottles B is made the same by a pitch alignment worm 5 provided before the medium harvesting and cleaning apparatus 6. A predetermined number (for example, four) of the roller bottles B sent by a pusher mechanism 6A on the medium harvesting and cleaning apparatus 6 and operatively connected to the pitch alignment worm 5, are sent by a roller bottle feeder 17 in groups of a predetermined number and in a direction perpendicular to the first supply conveyor 3 as shown in FIG. 4. The roller bottle feeder 17 is an extremely simple mechanism configured from a cam and a link mechanism (to be described later). The roller bottles B that have been tilted in a predetermined direction and sent, first have used medium withdrawn and removed from the inner surface of the roller bottles B by a liquid suction tube. Cleaning liquid is then supplied to inside the roller bottles B by a roller bottle inner surface cleaning apparatus 21, the suction cups of a roller bottle tilt and roll apparatus 19 adhere to top and side portions of the roller bottles B and tilt the bottles to a predetermined angle on a tilter plate as shown in FIG. 3. Those of the roller bottles B for which the suction force is cancelled, are then automatically and uniformly rotated in a predetermined direction and the inner surfaces of the roller bottles B are cleaned. The cleaning is performed so that the cleaning liquid comes into sufficient contact with those parts of the inner walls of the roller bottles B to which cells are adhered. When the cleaning for the predetermined number of the roller bottles B is finished, the roller bottles B are returned to the upright position by a roller bottle holder and are sent to the second supply conveyor 7 by a separately provided pusher mechanism. The pitch of the roller bottles B is then re-aligned by a pitch aligning worm 8 and a pusher mechanism 9A operatively connected to the pitch aligning worm 8 then transfers the roller bottles B to the medium filling apparatus 9.

Figure 5:
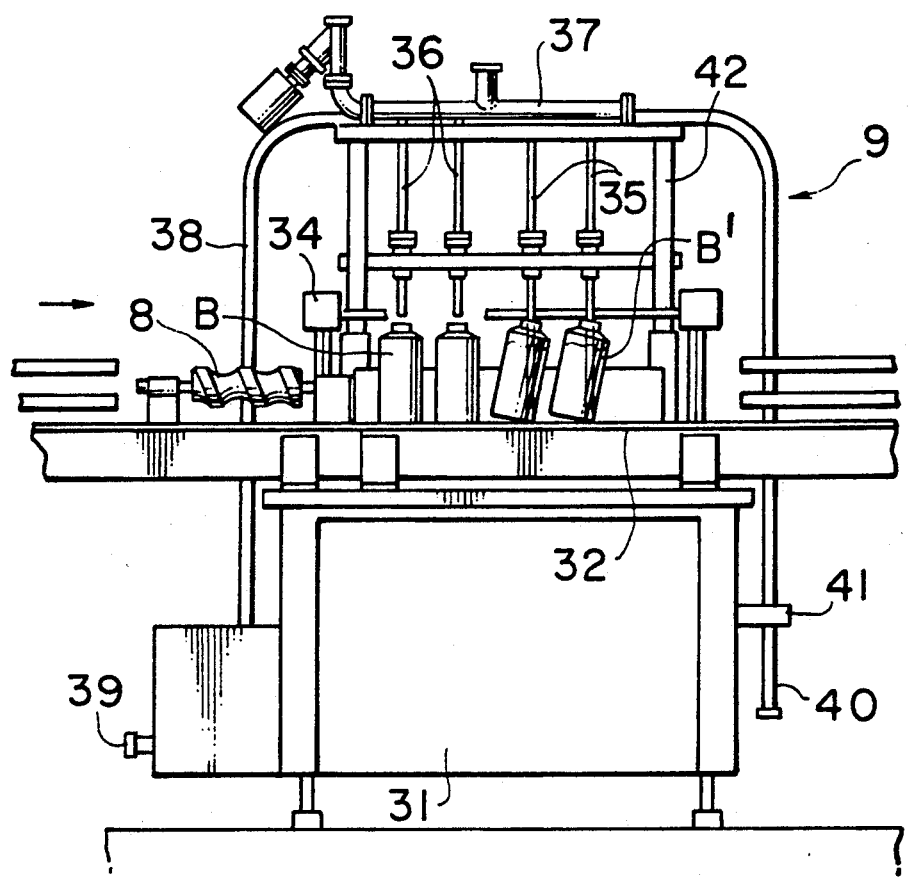
FIG. 5 is a front elevational view of the medium filling apparatus of the medium harvesting and cleaning apparatus according to the present invention.
Figure 6:
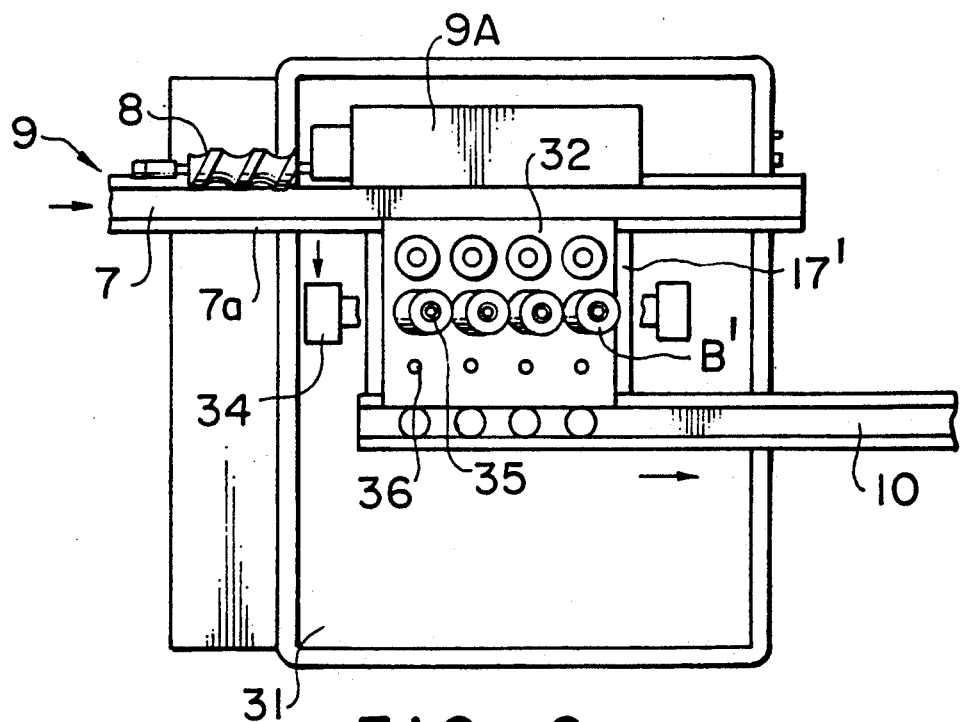
FIG. 6 is a plan view of the medium harvesting and cleaning apparatus according to the present invention.

The roller bottles B that have been sent in groups of a predetermined number and in a direction perpendicular to the second supply conveyor 7, in the same manner as they were sent beforehand to the medium harvesting and cleaning apparatus 6 by the bottle feeder 17 as shown in FIG. 3 and FIG. 4. The roller bottles B that have been tilted in a predetermined direction and sent, have cleaning liquid inside withdrawn and removed, are returned to the upright position and at the same time are filled with medium by a double nozzle for filling 36 as shown in FIG. 5 and FIG. 6. When the roller bottles B are filled, $CO_2$ is also introduced into the roller bottles B in order to adjust the pH value of the medium. The roller bottles B, for which these processes have been completed, are sent to a third supply conveyor 10, along which is provided a capper 11 which closes the caps of the roller bottles B. A cap hopper of the capper 11 supplies caps from the decapper 4. The roller bottles B which have been capped are then conveyed from inside the aseptic chamber 1 to a roller bottle turntable 12 provided outside of the aseptic chamber 1, and are conveyed by the rotation of the roller bottle turntable 12 to a culture chamber to be cultivated. Moreover, a control panel 13 for performing operation and control of the roller bottle filling and harvesting system according to this embodiment of the present invention, is provided at a suitable position external to the aseptic chamber 1.

This explanation of the mode of operation of an embodiment of a medium filling and harvesting system according to the present invention, has been given in the representative order of decapping→used medium withdrawing→filling with cleaning liquid→tilting and rotating roller bottles→cleaning liquid withdrawing-→medium filling→capping (B mode). However, it is also possible to select the following different combinations of processes according to necessity.

time. The roller bottles B are then capped and then sent to the following process for culture. In Mode C (medium harvesting process), the roller bottles B for which culture has been completed are supplied to this roller bottle filling and harvesting system and are decapped by the decapper 4, and the medium including the effective substances produced are then harvested from the roller bottles B by the medium harvesting and cleaning apparatus 6. The harvested medium is stored in tanks or the like. Furthermore, in Mode D (medium harvesting and exchange processes), the roller bottles B supplied to this roller bottle filling and harvesting system are decapped by the decapper 4, and the cultivated medium is then first of all harvested by the medium harvesting and cleaning apparatus 6. The roller bottles B are then filled again with fresh medium by the medium filling apparatus 9.

In this embodiment according to the invention, in order to remove and clean away used medium adhering to inner walls of the roller bottles, a cleaning liquid is introduced into the roller bottles which are then tilted through a predetermined angle from the upright position so that the cleaning liquid can come into sufficient contact with those parts of the inner walls of the roller bottles to which medium is adhered. The medium harvesting and cleaning apparatus 6 that rotates the roller bottles therefore has the configuration shown in FIG. 3 and FIG. 4. This is to say that the medium harvesting and cleaning apparatus 6 comprises a frame 15 mounted on a floor surface of an aseptic chamber 1, a horizontal table 16 at the same level as a roller bottles B conveyor surface of a first supply conveyor 3 and a second supply conveyor 7, and a roller bottle feeder 17 that sends a group of a predetermined number of (for example, four) roller bottles in a direction perpendicular to the first supply conveyor 3. On the frame 15 is provided a plural number of supporting columns 23 provided with withdrawing tubes 20 for withdrawing and removing used medium from the upright roller bottles B, and roller bottle inner surface cleaning apparatus 21 to supply cleaning liquid via a manifold 22 after the used medium have been withdrawn and removed. In addition, the frame 15 is also provided with a pusher 18 that tilts a line of roller bottles B in the position where the used

| Mode | Decapping | Withdrawl used medium or effective substance | Filling with cleaning liquid or medium | Process Roller table tilting & rotation, cleaning | Withdrawl cleaning liquid | Filling with medium or cell | Capping |
| --- | --- | --- | --- | --- | --- | --- | --- |
| A | O | → | O | → | → | O | O |
| B | O | O | O | O | O | O | O |
| C | O | O | → | → | → | → | O |
| D | O | O | → | → | → | O | O |

In this table, the "→" mark indicates a process which is omitted, in that the roller bottles pass by either the medium recovery and cleaning apparatus, and the medium filling apparatus.

This is to say that as shown in the table above for Mode A (only the cell inoculation process), the roller bottle filling and harvesting system according to the present invention supplies unused and closed roller bottles B. The roller bottles B are decapped by the decapper 4 and medium for the culture of cells are then filled in the roller bottles B by the medium harvesting and cleaning apparatus 6. Cell inoculation is also performed by the medium filling apparatus 9 at the same medium is withdrawn, in the direction as shown in the figures, to facilitates the withdrawing out and removal of the used medium from the bottom of the roller bottles B. Furthermore, the frame 15 is also provided with a roller bottle tilt and roll apparatus 19 having suction cups.

In a medium harvesting and cleaning apparatus 6 having this configuration, a pitch alignment worm 5 aligns the pitch of roller bottles B and a line of roller bottles B are guided by guide plate 3a and are transferred to horizontal table 16. The roller bottles B on the horizontal table 16 are intermittently sent in a direction perpendicular to the first supply conveyor 3, by the fingers of the roller bottle feeder 17 and then in order to facilitate the removal of used medium by the sucking tubes 20, are tilted through a predetermined angle by a tilter plate operatively connected to a pusher 18 provided in an upright position on the frame 15. (This is the status shown in B' of FIG. 3.) The roller bottles B for which the used medium have been completely sucked out, are then returned to the upright position by the pusher 18, and the fingers of the roller bottle feeder 17 then send the roller bottles B to a cleaning liquid introduction apparatus which inserts cleaning liquid into a plural number of bottles by a roller bottle inner surface cleaning apparatus 21. The suction cups of the roller bottle tilt and roll apparatus 19 attached to the roller bottles B for which the introduction of the cleaning liquid has been completed, tilt them, and rotate them for a predetermined time in order to clean them. The rotation of the line of the roller bottles B is stopped when the bottles are clean and the roller bottles B are then returned to the upright position and pushed to a second supply conveyor 7 by another pusher. Moreover, in this embodiment according to the invention, the medium filling apparatus 9 that withdraws the cleaning liquid of the cleaning agent out of the roller bottles B and supplied medium to inside the roller bottles B has the configuration shown in FIG. 5 and FIG. 6. This is to say that the medium filling apparatus 9 comprises a frame 31, a horizontal table 32 fixed at the same level as the roller bottle B conveying surface of a second supply conveyor 7 and a third supply conveyor 10 provided on frame 31, and a roller bottle feeder 17 that groups a predetermined number (for example, four) of the roller bottles B and sends them intermittently in a direction perpendicular to the direction of motion of the second supply conveyor 7. The frame 31 is provided with a plural number of supporting columns 42 provided with withdrawing tubes 35 for withdrawing and removing cleaning liquid from the upright roller bottles B, and double nozzles 36 for filling the roller bottles B simultaneously with medium and $CO_2$ gas via a manifold 37. Moreover, the $CO_2$ gas is supplied by $CO_2$ gas supply pipes 40 via a pinch valve 41 and functions to adjust the pH value of the medium. In addition, the frame 31 is provided with a pusher 34 to tilt the line of roller bottles B at the cleaning liquid withdrawing position, in the direction indicated in the FIG. 5 and FIG. 6, and therefore facilitate the withdrawing and removal of the cleaning liquid at the bottoms of the roller bottles B. The cleaning liquid withdrawn is discharged to outside of the system via discharge pipe 38 by a discharge outlet 39.

In a medium filling apparatus 9 having a configuration as described above, a pitch alignment worm 8 aligns the pitch of roller bottles B and a line of roller bottles B are guided by guide plate 7a and are transferred in the direction of the arrow in the figures, to a horizontal table 32 provided at the same level as the second supply conveyor 7. The roller bottles B on the horizontal table 32 are intermittently sent in a direction perpendicular to the supply conveyor 7, by the fingers of the roller bottle feeder 17 and are sent to the withdrawing position where the cleaning liquid inside the bottles is withdrawn by withdrawing tubes 35. The cleaning liquid that is withdrawn and removed is discharged by discharge pipe 38. When this is done, in order to facilitate the removal of cleaning liquid by the withdrawing tubes 35, the roller bottles B are tilted through a predetermined angle by a pusher 34. (This is the status shown in B of FIG. 5.) After the bottles B' have had the cleaning liquid withdrawn, they are returned to the upright position by pusher 34, sent to the medium filling position by the fingers of roller bottle feeder 17', and have $CO_2$ gas introduced into them by double nozzles 36 for filling. The roller bottles B for which the filling with medium is finished, are sent by the fingers of roller bottle feeder 17', and are pushed in the direction indicated by the arrow in the figure, onto a third supply conveyor 10.

The present invention has the configuration as described above and so can perform automatic and high-speed processing for the filling, cleaning and exchange, and cell inoculation for serum cultivation in roller bottles in an unmanned and aseptic environment. In addition, the configuration of the roller bottle filling and harvesting system is extremely simple and its control can be performed very easily. Moreover, it is possible to freely select the arrangement of the apparatus configuring this roller bottle filling and harvesting system in accordance with the configuration of the aseptic chamber, and the desired operating mode can also be selected.

Furthermore, sterilization and cleaning of the roller bottles can be easily performed and extremely clean walls of the roller bottles can be expected. In addition, it is also possible to control the amount of $CO_2$ gas used for flushing, to an extremely high precision. The system is one for the unmanned filling and harvesting of medium and so contamination due to microorganisms carried on the human body can be significantly reduced, a high and uniform productivity of the object substances can be expected and the medium filling and harvesting processes can be fully automated. Still furthermore, the medium filling amount is recorded for each of the bottles and so all bottles having other than the set amount can be automatically excluded as faulty products. Moreover, it is possible to perform data management using a separately provided measuring and recording apparatus.

Roller bottle feeder

In this embodiment according to the present invention, the roller bottle feeder 17 that feeds the roller bottles B has the configuration as described below.

Figure 7:
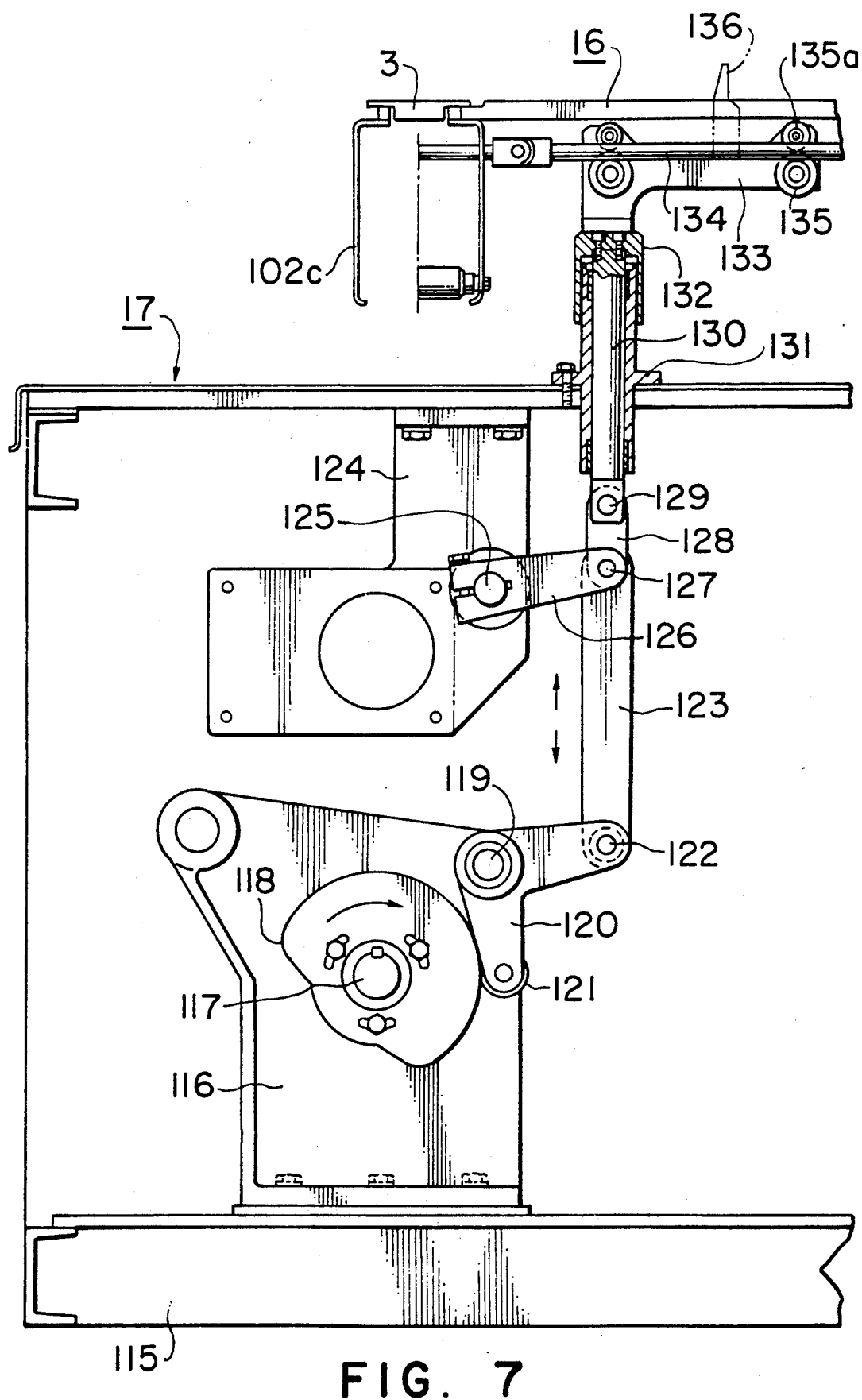
FIG. 7 is a front elevational view of the bottle feeder of the medium harvesting and cleaning apparatus according to the present invention.
Figure 8:
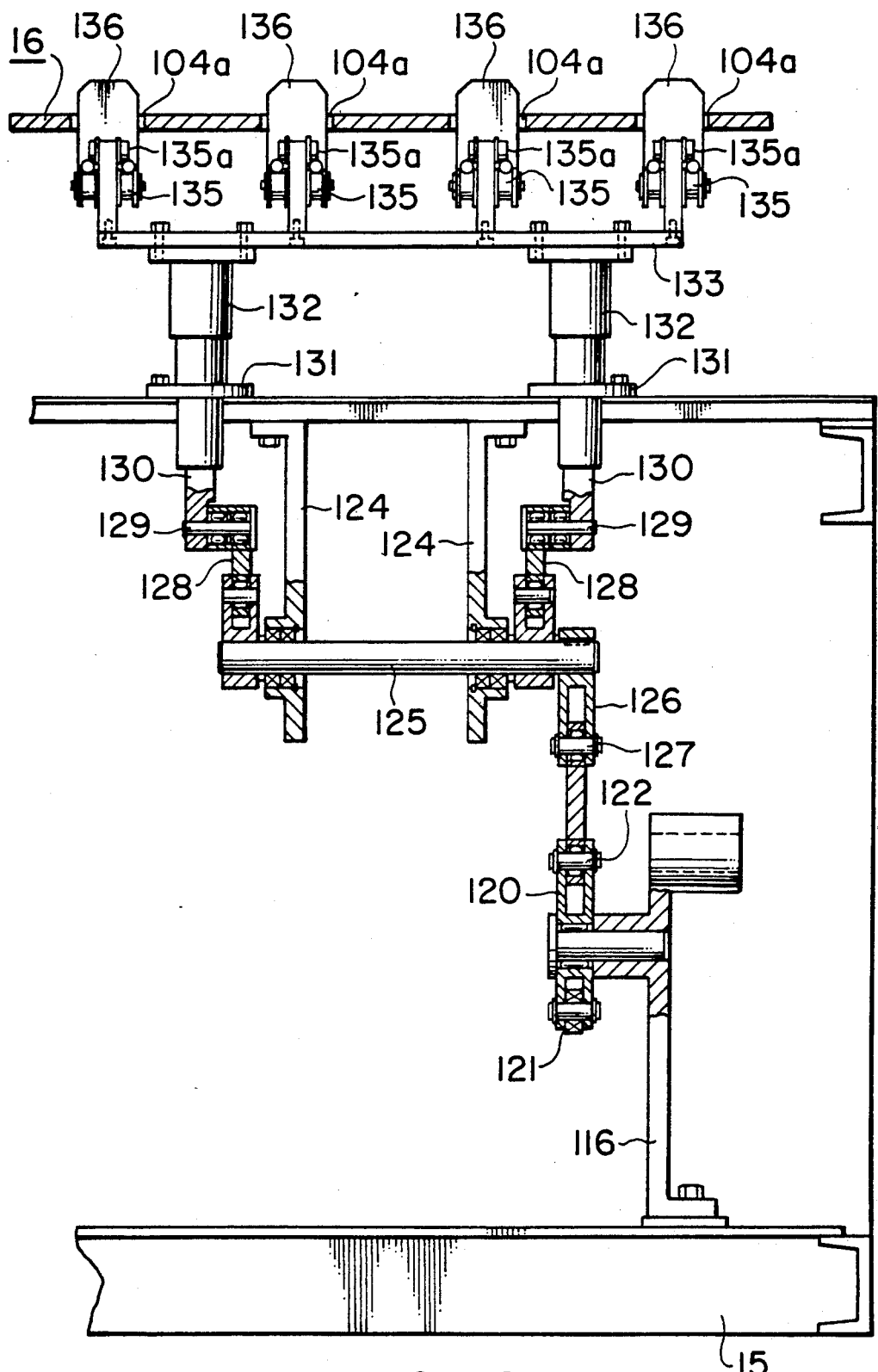
FIG. 8 is a side elevational view of the bottle feeder of the medium harvesting and cleaning apparatus according to the present invention.

As shown in FIG. 7 through FIG. 10, the roller bottle feeder 17 of this embodiment according to the invention comprises a bottle feed lever raising and lowering member, and a bottle feed lever member. As shown in FIG. 7 and FIG. 8, the bottle feed lever raising and lowering member comprises a frame 115 fixed to a floor of an aseptic chamber, and a bracket 116 screwed to the frame 115. To the middle of the bracket 116 is pivotably mounted a drive shaft 117 which is operatively connected to a separately provided drive motor (not shown in the figures) and to which is fixed a raising and lowering cam 118. Moreover, an L-shaped lever 120 is pivotably mounted via a support pin 119 to a right end portion of the bracket 116, and one end of the L-shaped lever 120 has a rotating roller 121 pivotably mounted and in contact with a flywheel of raising and lowering cam 118, and another end having a pin 122 pivotably mounted thereon. Furthermore, two brackets 124 are suspended from an upper surface of frame 115 and pivotably support a support shaft 125 at both its ends. To the support shaft 125 is fixed a rocking lever 126. A raising and lowering link 123 is axially supported between pin 127 which is pivotably mounted to a free end of the rocking lever 126, and pin 122 which is pivotably mounted to a free end of the L-shaped lever 120 so that the rising and falling action of the L-shaped lever 120 is transmitted to a connecting link 128 that has one end pivotably mounted to both the rocking lever 126 and the raising and lowering link 123, and the other end pivotably mounted to a raising and lowering shaft 130 via a pin 129. The raising and lowering shaft 130 is axially supported by bearing cylinder 131 fixed to an upper surface of raising and lowering shaft 130 and an upper open portion of the bearing cylinder 131 is covered by a lid sleeve 132. A roller support bracket 133 is fixed to the lid sleeve 132 and auxiliary roller 135a and support roller 135 pivotably mounted to roller support bracket 133 support a tact rod 134 of a bottle feed lever 136 so as to be freely movable in the horizontal direction. A plural number of roller bottle feed levers 136 are movable inside slits 104a provided in a horizontal table 16 provided at the same level as a conveyor surface of a supply conveyor 3.

Figure 9:
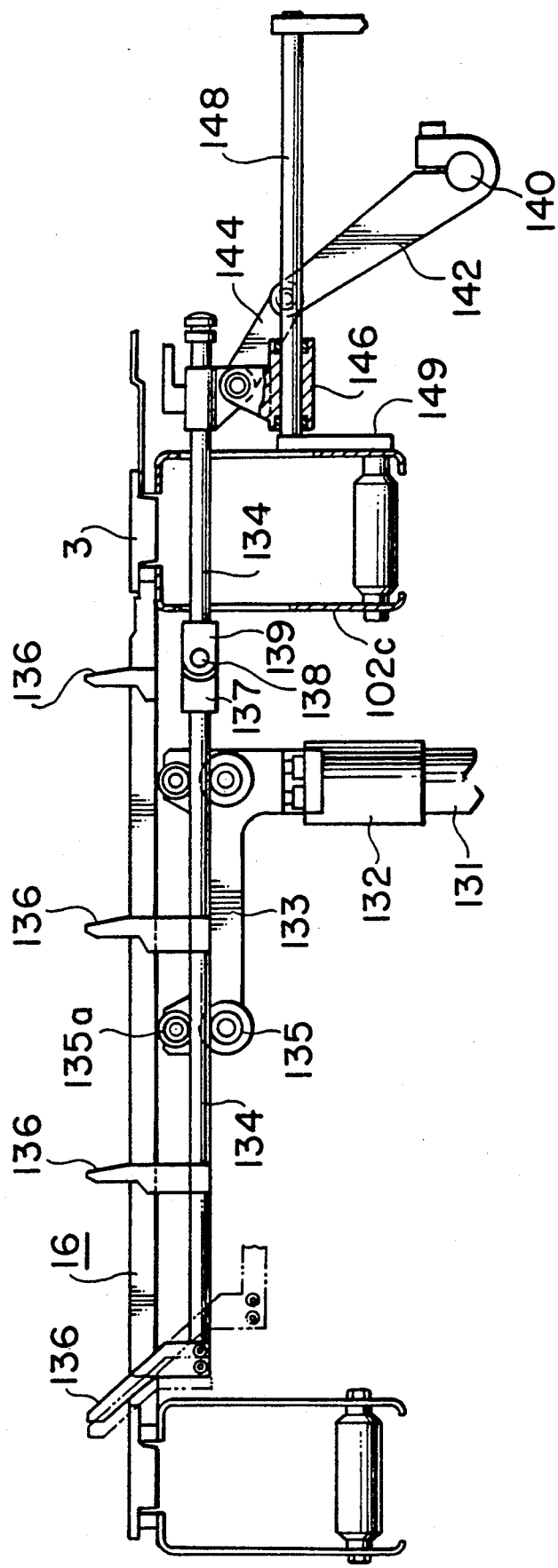
FIG. 9 is a side elevational view of the holder of the bottle feeder of the medium harvesting and cleaning apparatus according to the present invention.
Figure 10:
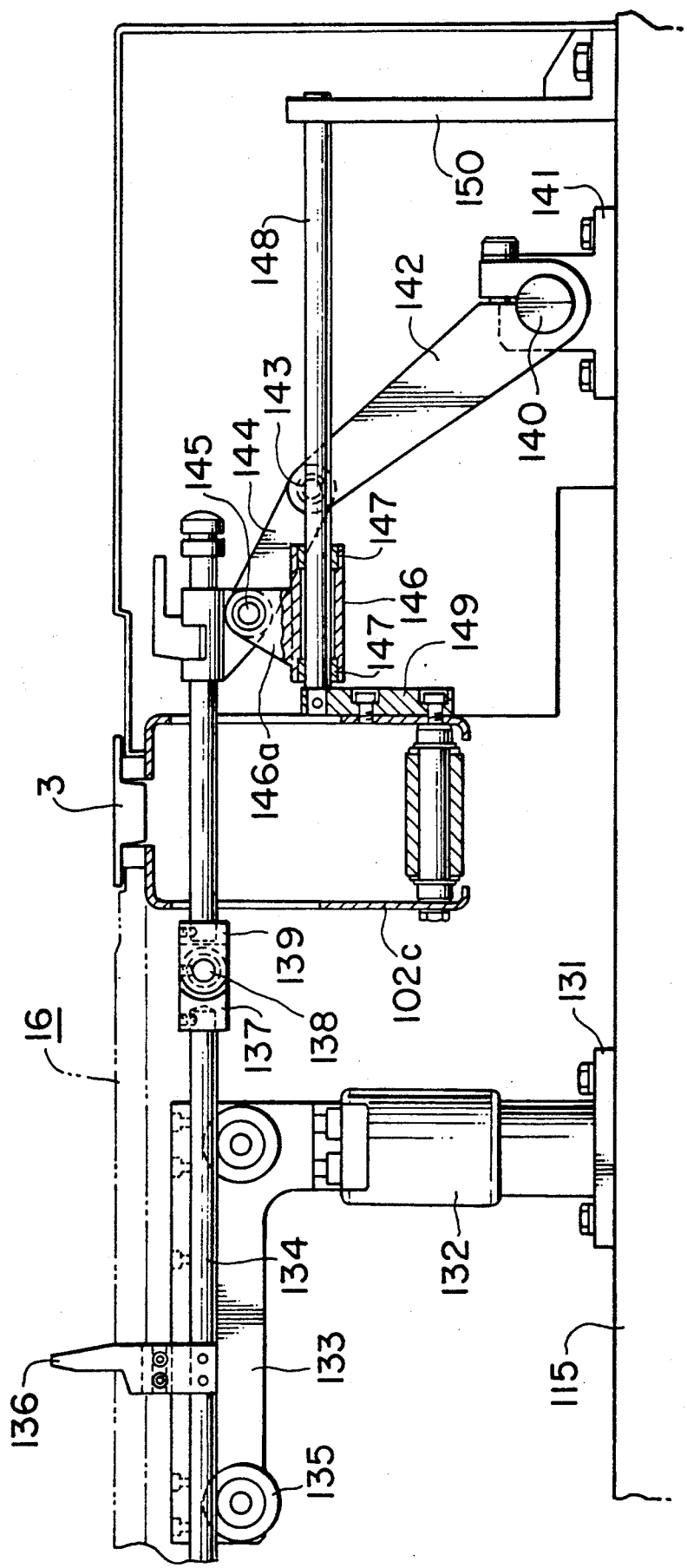
FIG. 10 is an enlarged view of the main portion of the bottle feeder of the medium harvesting and cleaning apparatus according to the present invention.

Furthermore, as shown in FIG. 9 and FIG. 10, a bottle feed lever member is rotatably supported at one end by the support roller 135 and the auxiliary roller 135a, is interconnected via a pin 138 to couplings 137 and 139, and comprises a tact rod 134 fixed to moving sleeve 146. A plural number of bottle feed levers 136 are mounted to the tact rod 134. The moving sleeve 146 is mounted to a guide rod 148 via two bushes 147 and so as to be freely movable, and both ends of the guide rod 148 are supported by a bracket fixed to the frame 115 and a holder 149 fixed to a side surface of support channel 102c of the supply conveyor 3. Another end of the tact rod 134 and a rib member 146a of the moving sleeve 146 are pivotably mounted to a shared pin 145. One end of a connector lever 144 is pivotably mounted to the shared pin 145 and another end of connector lever 144 is pivotably mounted to rocker lever 142 via a pin 143. A bearing part of the rocker lever 142 is fixed to a bottle feed lever drive shaft 140 pivotably mounted in bearing bracket 141 fixed to the frame 115. The bottle feed lever drive shaft 140 is mechanically interconnected to a separate feeder cam fixed to drive shaft 117 via a separately provided link mechanism, and the movement of the feeder cam rocks the bottle feed lever drive shaft 140 through a predetermined angle in the horizontal direction.

Figure 11:
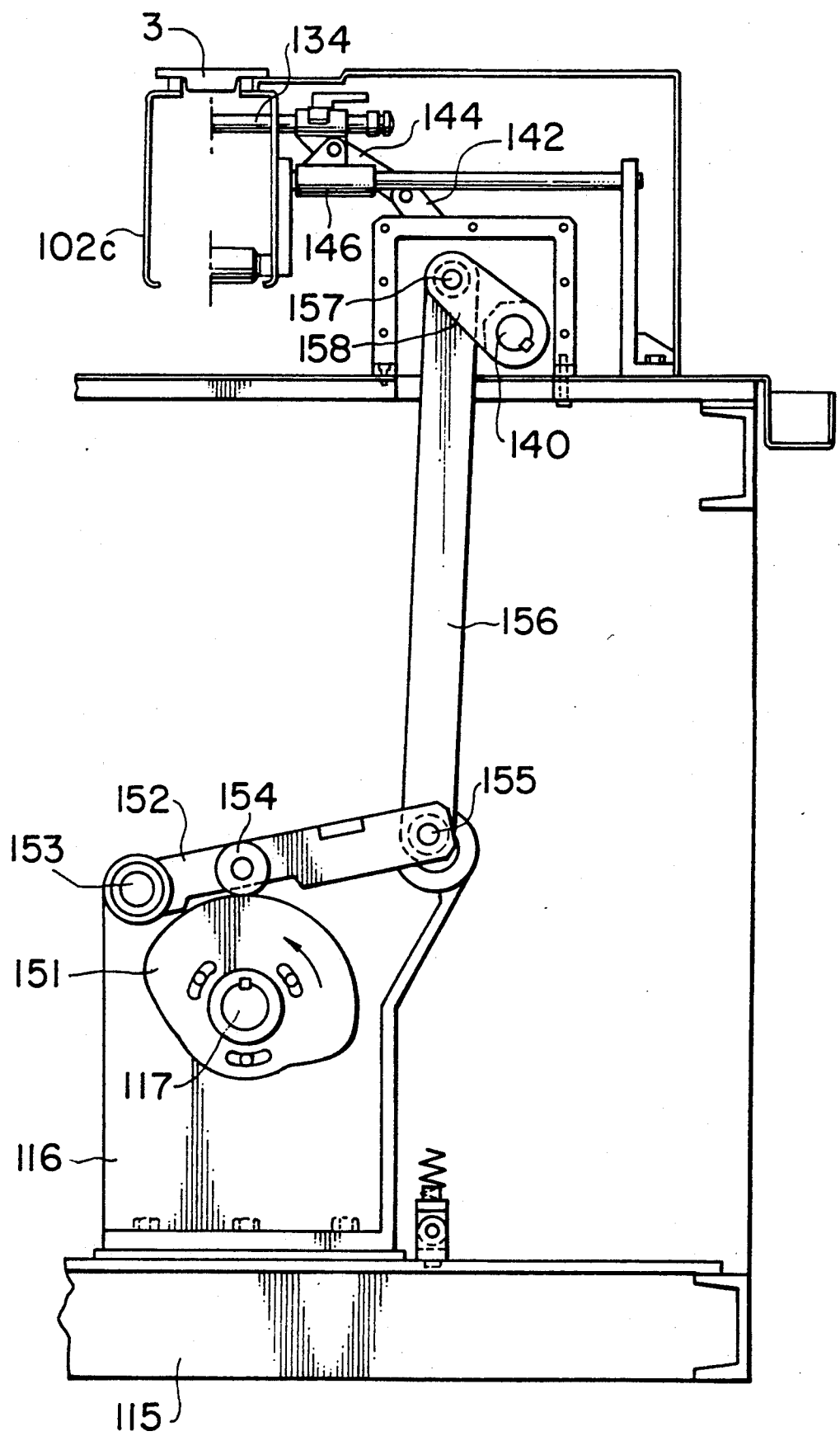
FIG. 11 is a detailed view of the tact movement part of the tact rod of the bottle feeder of the medium harvesting and cleaning apparatus according to the present invention.
Figure 12:
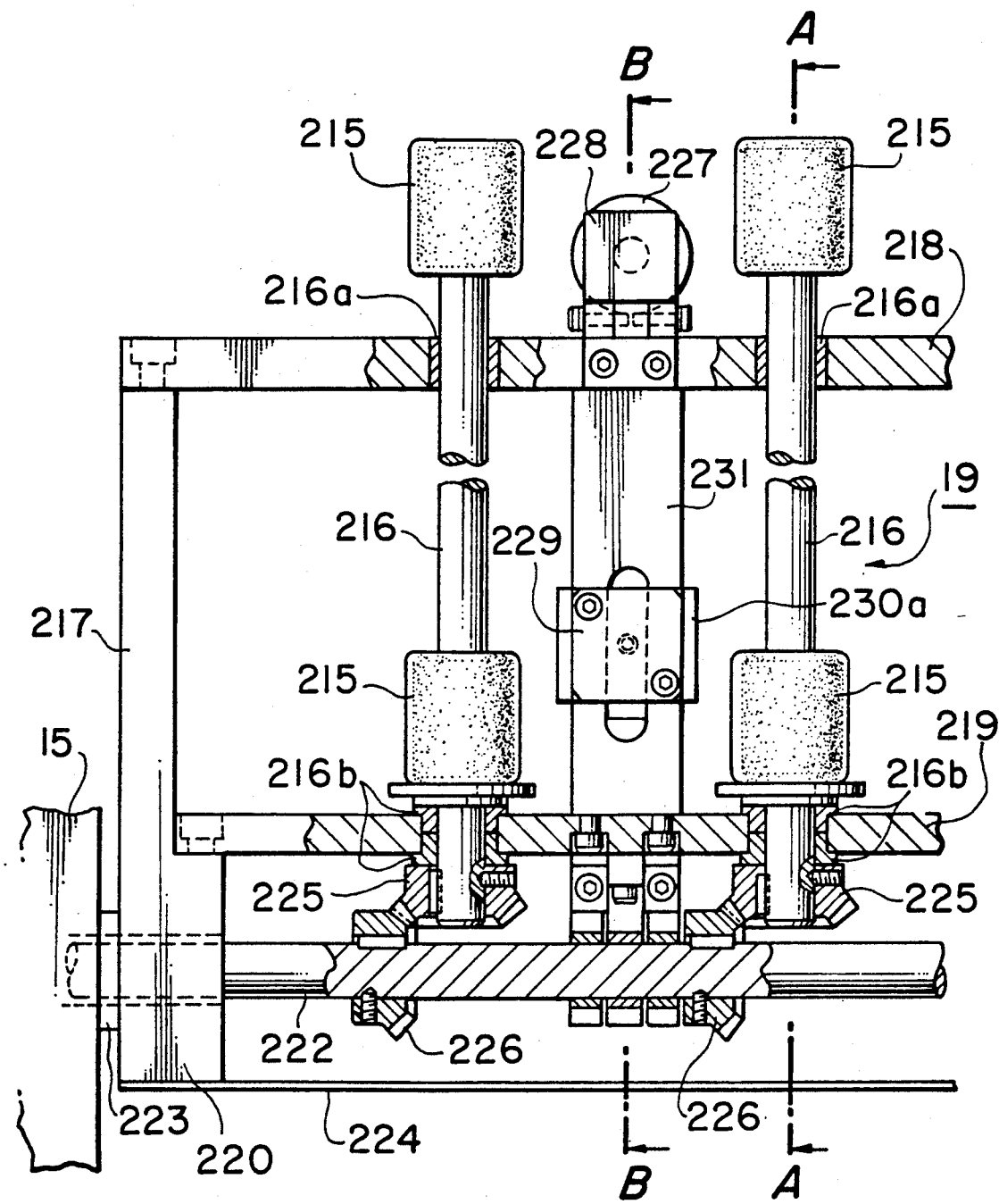
FIG. 12 is a front elevational view of the roller bottle tilt and roll apparatus of the medium harvesting and cleaning apparatus according to the present invention.

The following explanation relates to the rocker mechanism of the bottle feed lever drive shaft 140. As shown in FIG. 11, the rocker mechanism comprises a feeder cam 151 mounted to a drive shaft 117 pivotably mounted to a bracket 116 fixed to the frame 115. A profile surface of the feeder cam 151 is in rolling contact with a roller 154 axially supported by a connector link 152 pivotably mounted by a boss member of an upper end of the bracket 116 by a pin 153 fixed thereon. The movement of the feeder cam 151 is transferred to feeder link 156 supported by a pin 155 at a free end of connector link 152. Furthermore, feeder link 156 is pivotably mounted to a connector 158 fixed to bottle feed lever drive shaft and to a pin 157 at a free end of the connector 158.

With this configuration, the movement of a profile surface of feeder cam 151 is transferred to the bottle feed lever drive shaft 140 via feeder link 156 and connector 158, and the rocker lever 142 fixed to the bottle feed lever drive shaft 140 is rocked to a predetermined angle, the result of which is the reciprocal motion of the tact rod 134.

The roller bottle feeder 17 of this configuration then operates as follows to sequentially perform to tact feed roller bottles B. This is to say that the drive motor mechanically linked to drive shaft 117 rotates and raising and lowering cam 118 fixed to the drive shaft 117 rotates accordingly and at a predetermined speed in the direction indicated by the arrow as shown in FIG. 7. The rotation of the raising and lowering cam 118 is transmitted via the roller 121 to the L-shaped lever 120, one end of which rotates in the anticlockwise direction, and another end of which is connected via the pin 122 to the raising and lowering link 123 which rises by the amount of stroke (30 mm, for example) regulated by the rocker lever 126. Through this action, the raising and lowering shaft 130 guided by bearing cylinder 131 and pivotably mounted to the raising and lowering link 123 via the connecting link 128, rises in accordance with a predetermined stroke and makes bottle feeder levers 136 fixed to the tact rod 134 rise from and sink into slits 104a in the horizontal table 16. On the other hand, a separately provided cam on the drive shaft 117, rocks the bottle feed lever drive shaft 140 a predetermined angle in the horizontal direction and in phase with the raising and lowering cam 118, and this rocking movement is transferred to the rocking lever 142. Due to the action of the connector lever 144 pivotably mounted to the rocker lever 142, the tact rod 134 is guided by the support roller 135 and the auxiliary roller 135a and has reciprocal motion at a predetermined cycle imparted to it in the horizontal direction. Because of this, the cyclic vertical motion and the cyclic horizontal motion of the tact rod 134 combine to become the tact motion, and the bottle feed lever 136 moves intermittently to pull in roller bottles B loaded upright on the horizontal table 16, sink into the slits in the horizontal table 16, and then rise once again at periodic intervals to feed bottles intermittently and horizontally.

This roller bottle feeder has a configuration as described above and so when roller bottles are filled with serum medium or the like, cleaned and exchanged, and have cell inoculation performed by this roller bottle filling and harvesting system in an unmanned and aseptic environment, the roller bottle feeder can continuously perform to tact feed a series of roller bottles (four, for example) accurately and promptly to the cleaning and filling positions of the roller bottles at the medium harvesting and cleaning apparatus or the medium filling apparatus. The feeder uses cams and links and the like instead of air cylinders or other compressed air apparatus and so it is possible for the roller bottles to be handled gently. Through the use of the roller bottle feeder according to the present invention, it is possible to configure an unmanned filling and harvesting system for roller bottles to give the effects of significant reduction in microorganism contamination due to human carriers, a high-quality of the object substance, uniform productivity, and complete automation for the medium filling and harvesting processes. Moreover, the roller bottle feeder has a comparatively simple mechanism and so the manufacturing cost can be reduced, and maintenance and repairs facilitated. Furthermore, the roller bottle feeder according to the present invention is not limited in application to roller bottles but can also be used as an apparatus for the tact feed of products of other shapes.

Roller Bottle Tilt and Roll Apparatus

The following is an explanation of the roller bottle tilt and roll apparatus of one embodiment of the present invention, with reference to FIG. 12 to FIG. 15. The main body of the roller bottle tilt and roll apparatus 19 that has a vacuum pad 227 that holds and supports the roller bottles B, is pivotably supported in the frame 15 of the medium harvesting and cleaning apparatus 6 by a support plate tilting shaft 223 at both its ends so as to be freely rotatable to a predetermined angle. Support plates 218 and 219 are supported by a boss member 220 fixed to this support plate tilting shaft 223, and two roller shafts 216 having rubber rollers 215 that are freely rotatable and that support the bottles when they are tilted, are mounted via bushes 216a and 216b so as to be freely rotatable. Moreover, a drive shaft 222 rotated by a separately provided motor and freely inserted into the support plate tilting shaft 223 and passing through the boss member 220, is in engagement with a bevel gear 225 fixed to one end of a roller 216 fixed to another bevel gear 226, so as to transmit the rotation of the drive shaft 222 to the roller shafts 216. Moreover, the drive shaft 222 is covered by a cover plate 224, and the support plates 218 and 219 have another support plate 231 fixed to them and to this support plate 231 is mounted a vacuum pad 227 and a roller bottle pusher 229. The vacuum pad 227 is mounted to the end of a jig cylinder 228 fixed to the support plate 231, and the inner member of a vacuum sleeve 227a is connected to a vacuum source via a nipple 227b. Through this arrangement, it is possible for the roller bottles B to move slightly when the vacuum pad attaches to them and also for the roller bottles B to be attached by the suction force of the vacuum source. The required number of (for example, four) roller bottle tilt and roll apparatus 19 having such a configuration is provided in a line.

Figure 13:
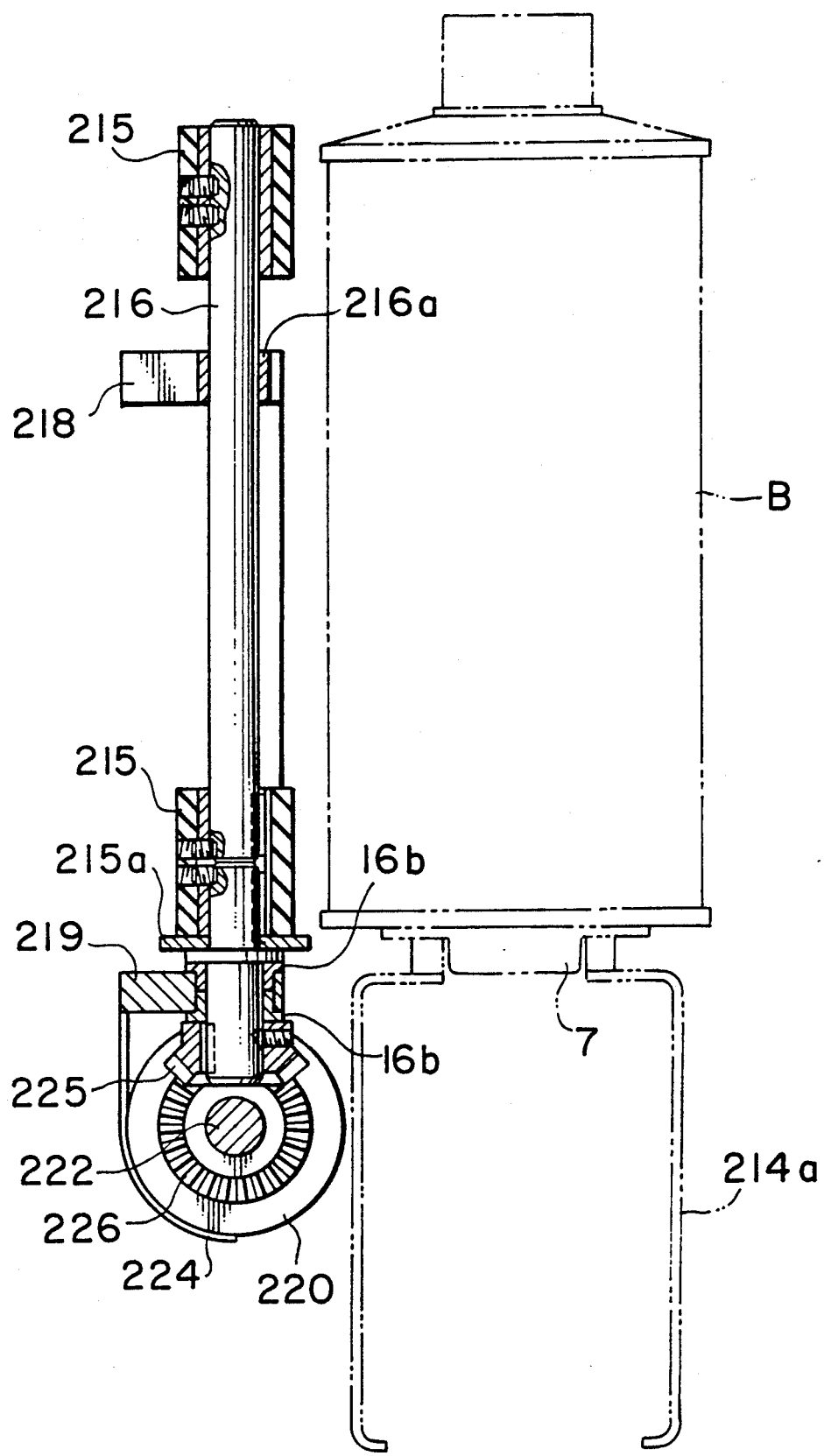
FIG. 13 is a sectional view along section lines A—A of FIG. 12, indicating the state where the roller bottles are in the upright position.
Figure 14:
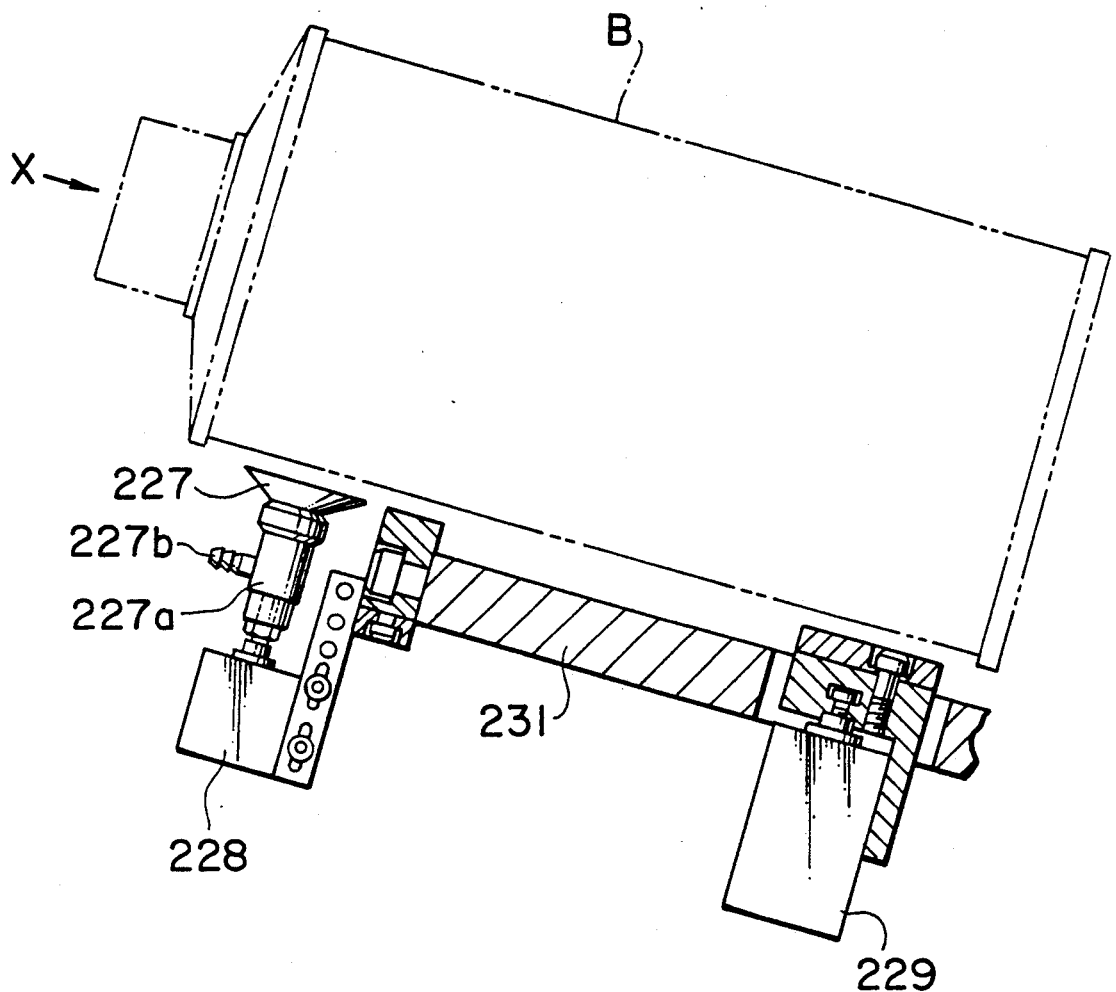
FIG. 14 is a sectional view along section lines B—B of FIG. 12 indicating the state where the roller bottles are in the tilted position.
Figure 15:
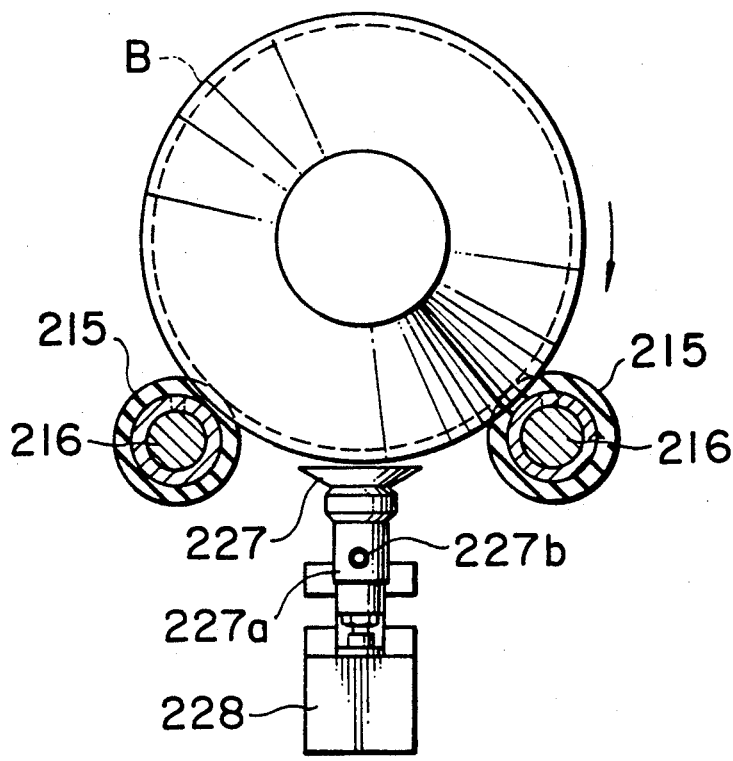
FIG. 15 is a view from the X direction of FIG. 14, showing the state where the bottles are held.

A series of roller bottles B that have been cleaned are sent by the roller bottle feeder 17 to the roller bottle tilt and roll apparatus 19 having such a configuration. At the roller bottle tilt and roll apparatus 19, the side surfaces of the roller bottles B in the upright position shown in FIG. 13, are sucked by the vacuum pad 227 and held by the roller bottle holder 230, are tilted by the support plate tilting shaft 223 to the position as shown in FIG. 14. At this position, the suction force of the vacuum pad 227 is cancelled by the jig cylinder 228 and the bottles are rolled in the required direction for a predetermined time by the two rubber rollers 215 and the inner surfaces of the bottles are given a forced cleaning. After the cleaning has finished, the rotation of the rubber rollers 215 stops and the roller bottles B are again sucked by the vacuum pad 227 while the rotation of the support plate tilting shaft 223 returns the roller bottles B to the upright position. Once the line of bottles has been returned to the upright position, the roller bottle pusher 229 sends the series of roller bottles B that have been cleaned, to the second supply conveyor 7 to send them to the following process. This series of operations is controlled by a control circuit having built-in solenoids and limit switches, and is performed automatically and continuously, and in phase with the other operations.

The roller bottle filling and harvesting system according to an embodiment of the present invention has the configuration as described above and so can perform automatic and continuous high-speed cleaning of roller bottles for medium culture and under unmanned and aseptic conditions. Moreover, the roller bottle filling and harvesting system according to the present invention uses rubber rollers as the drive source and so the entire system can be made compact. As a result, the system requires less installation space than conventional systems. Furthermore, the roller bottles can be rotated at high speed so that a significant increase is gained for the cleaning performance. Still furthermore, special and complex machinery is not used and so the control, inspection and repair of the overall system is facilitated.

Roller Bottle Inner Surface Cleaning Device

Figure 16:
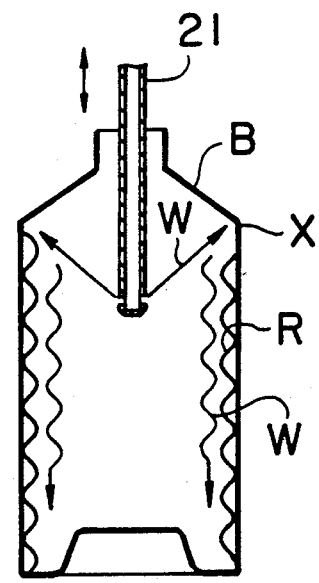
FIG. 16 is an outline view indicating the principle of cleaning the roller bottles by the cleaning liquid introduction nozzle of the roller bottle inner surface cleaning apparatus of an embodiment of the roller bottle filling and harvesting system according to the present invention.

The drawings show an embodiment of a roller bottle inner surface cleaning apparatus according to the present invention. As shown in FIG. 16, in the roller bottle inner surface cleaning apparatus according to the present invention, a roller bottle inner surface cleaning apparatus 21 provided on the medium harvesting and cleaning apparatus 6 of the medium filling and harvesting apparatus, is inserted in a roller bottle B and sprays cleaning W from the bottom end of the nozzle and in the upwards direction and cleans and removes the used medium that is adhered to the inner surface of the bottle. When this is done, the places where the cleaning liquid sprayed from the end portion of the nozzle, comes into contact with the inner surface of the roller bottles B are the neck portions (marked X in FIG. 16) where the cylindrical portions of the roller bottles meet the taper part of the neck. By the use of a configuration such as this, the sprayed cleaning liquid W is uniformly distributed around the inner surfaces of the roller bottles and strikes the previously mentioned neck portions (marked X), bounces back off them and falls slowly and evenly down the inner surfaces of the roller bottles B. The slow speed enables it to clean off and remove only the used medium adhering to the inner 5 surfaces of the bottles, while cells R remain on the inner surfaces.

Figure 18:
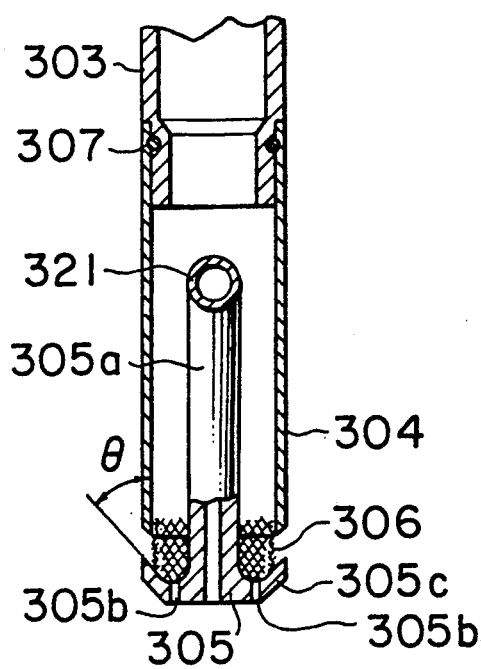
FIG. 18 is an enlarged view of the main portion of the cleaning liquid introduction nozzle of the roller bottle inner surface cleaning apparatus of an embodiment of the roller bottle filling and harvesting system according to the present invention.
Figure 17:
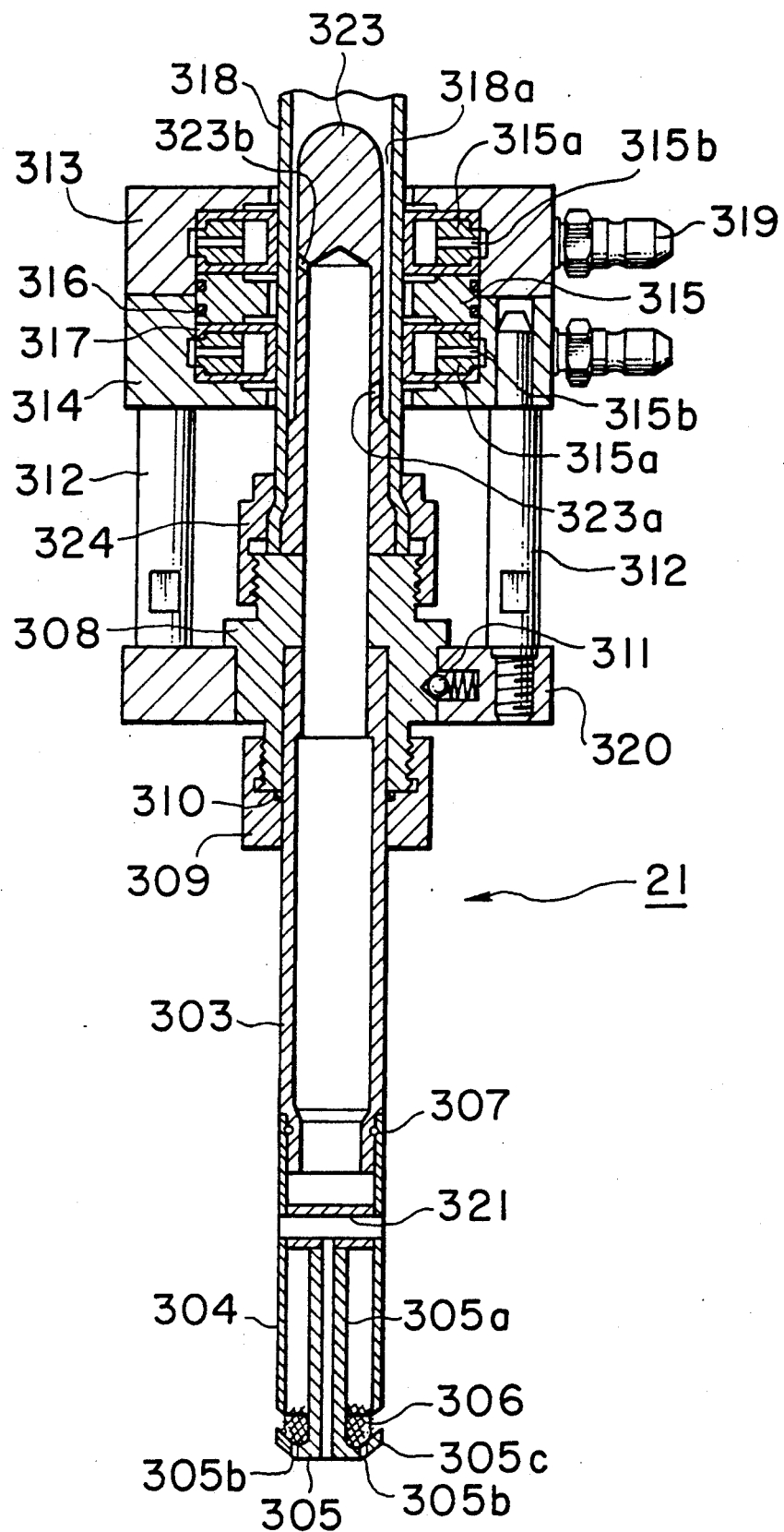
FIG. 17 is a longitudinal sectional view of the roller bottle inner surface cleaning apparatus.

The following is an explanation of the structure of an embodiment of the roller bottle inner surface cleaning apparatus according to the present invention, with reference to the drawings. As is shown in FIG. 17, the roller bottle inner surface cleaning apparatus 21 comprises a cleaning liquid introduction nozzle, and a nozzle support member. The roller bottle inner surface cleaning apparatus comprises a nozzle sleeve connected watertightly via an O-ring 307, to an end of a cleaning liquid introduction tube 303 that extends outwards, and a fixed nozzle tube 305 connected to a nozzle sleeve 304 via a bend 321. The bevelled part 305c of the nozzle tip 305 is provided with air bleed holes 305b and between the end portion of the nozzle sleeve 304 and the bevelled portion of the nozzle tip 305 is placed a strainer 306 of metal mesh of about 100 to 200 mesh. As shown in FIG. 18, the bevelled part 305c of the nozzle tip 305 is inclined upwards at an angle $\theta$ (20° to 80°) so as to spray cleaning liquid through the gaps in the strainer 306 and to direct it upwards at a predetermined angle. Moreover the stem 305a of the nozzle tip 305 is in midair and so the end part is connected by welding or the like, to the bend tube 321 mounted to the nozzle sleeve 304, so as to be intercommunicated with the bend hole of the bend tube 321.

The nozzle support member comprises a support plate 320 fixed to the frame of the roller bottle inner surface cleaning apparatus, a lower valve case 314 interconnected with the support plate 320 via a support column 312, and an upper valve case 313 screwed to the lower valve case 314. A connector collar 308 is fixed to the support plate 320 via a ball and plunger 311, and the lower portion of this connector collar 308 supports a cleaning liquid introduction tube 303 that is screwed into a tightening nut 309 via an 0-ring 310. Chuck rubbers 317 held by a fixing fitting 315 having a small hole 315b, is inserted between the upper valve case 313 and the lower valve case 314 via a collar 316, and each of the chuck rubbers 317 are connected to nipples for the supply of compressed air. Moreover, silicon tubes 318 are inserted into the inner diameters of the chuck rubbers 317 and hold the silicon tubes 318 and function as pinch valves. An air tube 323 is inserted into the inside of silicon tube 318 so that a gap 318a is formed between the outer wall of the air tube 323 and the inner wall of the silicon tube 318. The silicon tube 318 and the lower end of the air tube 323 are fixed to a collar 308 by connector nut 324. Furthermore, through holes 323a and small holes 323b are opened at suitable places in the air tube 323. Through this configuration, the cleaning liquid supplied by the cleaning liquid supply portion at the base of the silicon tube 318 flows into the gap 318a between the outer wall of the air tube 323 and the inner wall of the silicon tube 318, is led to inside the cleaning liquid introduction tube 303 by the small holes 323b and the through holes 323a opened in the air tube 323, flows through the strainer 306 placed across the guide switch 304 and the nozzle tip 305, and is sprayed upwards at a required angle $\theta$ (20° to 80°). (For example, if the water pressure is 0.1 to 0.3 kg/cm$^2$, then the water volume becomes 10 lit./min.) Foreign matter in the cleaning liquid is removed and the cleaning liquid flows and is sprayed evenly. In addition, sufficient air bleeding is performed by the air bleed holes 305b of the bevelled part of the nozzle nut 305 and the midair hole of the stem of the nozzle tip 305.

Moreover, in order to adjust the quantity of cleaning liquid, the compressed air from the compressed air supply nipple 319 passes through the either the small holes 315b of the fixing fitting 315a or both the air chambers of the chuck rubbers 317, to expand the chuck rubbers 317 and deform the inner side of the silicon tube 318.

Furthermore, the roller bottle inner surface cleaning apparatus 21 according to an embodiment of the present invention has such a configuration so that when the cleaning liquid introduction nozzle is inserted into the roller bottles B and cleaning of the roller bottle inside walls is performed, the sprayed cleaning liquid strikes the inner surfaces of the roller bottles B at the neck portions (marked X in FIG. 16) where the cylindrical portions of the roller bottles meet the taper part of the neck. As a result, the cells that are adhered to the inner surface of the roller bottles B remain as they are, and the used culture medium that covers them is removed and cleaned away.

Moreover, the gap between the end of the guide sleeve and the nozzle tip can be adjusted to regulate the supply pressure of the cleaning liquid.

This roller bottle inner surface cleaning device has the configuration as described above and the cleaning liquid has contained foreign matter removed by a strainer, and is sprayed uniformly. The cleaning liquid can therefore be uniformly sprayed on the inner surfaces of the roller bottles and made to fall down the inner surfaces slowly along them so that an excellent cleaning effect can be expected. As a result, the cells that are adhered to the inner surface of the roller bottles B remain as they are, and the used culture medium that covers them is removed and cleaned away. Furthermore, it is not necessary to tilt or rotate the roller bottles and so the structure of the cleaning apparatus itself can be simplified and made more compact. Therefore, it is possible to perform continuous and high-speed cleaning of the inner surfaces of roller bottles.

Medium and $CO_2$ Simultaneous Introduction Nozzle

Figure 19:
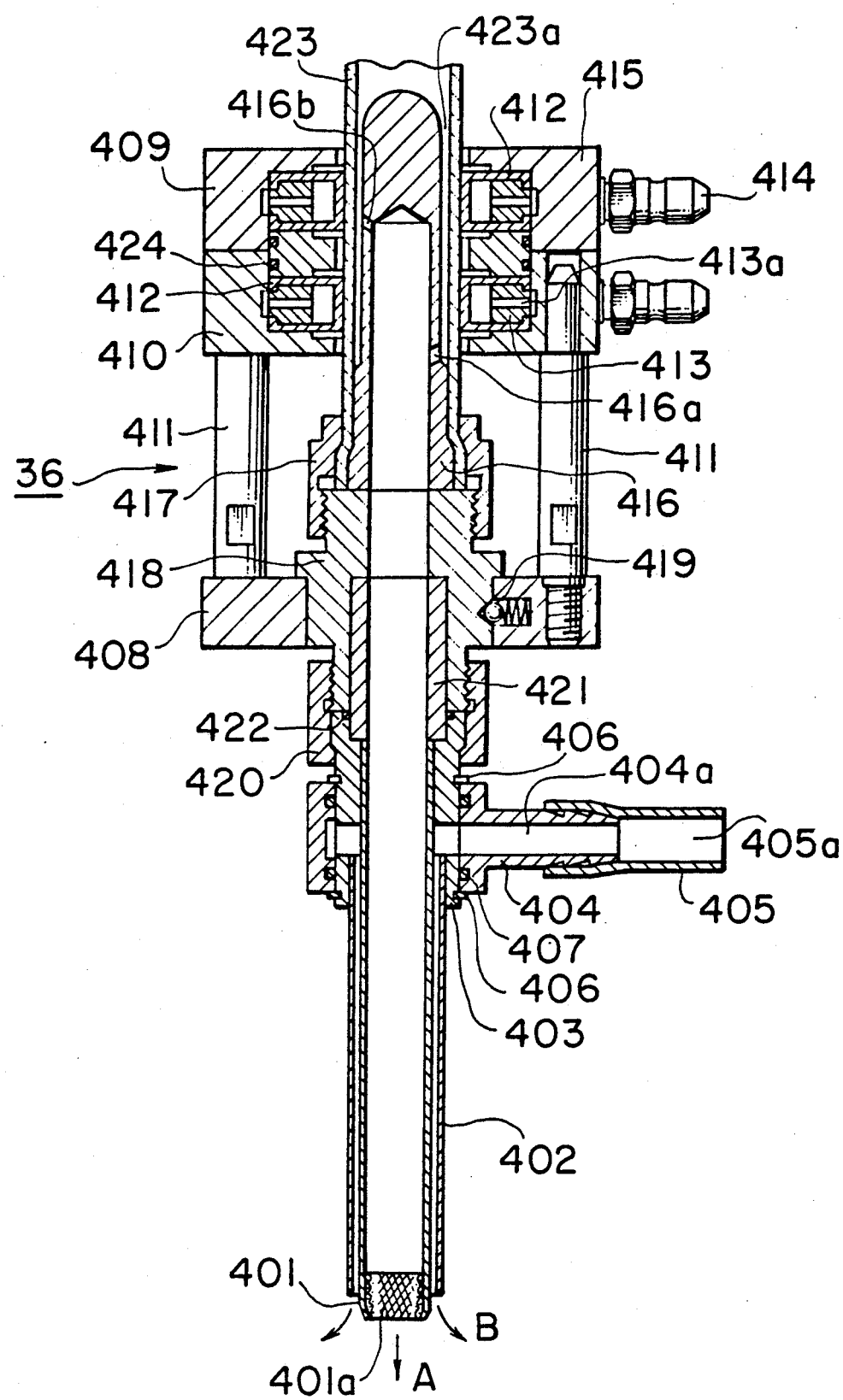
FIG. 19 is a longitudinal sectional view of the double nozzle for the simultaneous introduction of the medium and $CO_2$ gas, of the roller bottle filling and harvesting system according to the present invention.
Figure 20:
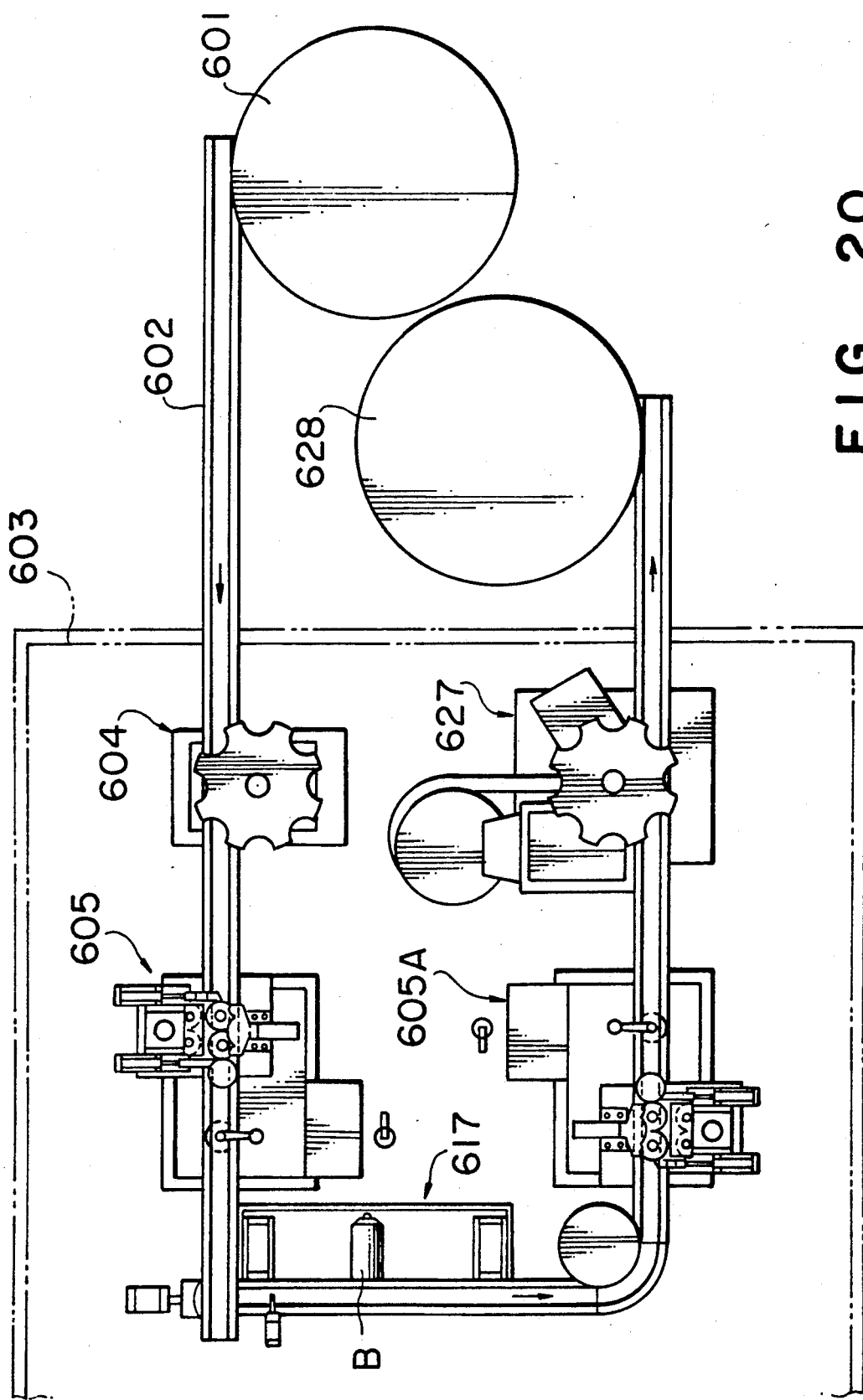
FIG. 20 is a plan view of a conventional roller bottle filling and harvesting system.

This embodiment of the double nozzle 36 for the simultaneous introduction of the culture medium and $CO_2$ comprises an inner nozzle 401 comprising a tube body having a strainer 401a of fine metal mesh at the end portion indicated in FIG. 19, and an outer nozzle 402 comprising a tube body disposed coaxially with respect to the inner nozzle 401 and so as to form a gap between it and inner nozzle 401. A manifold 404 of a $CO_2$ gas nozzle 403 and through holes 404a and 405a of a silicon tube 405 are interconnected with this gap. The manifold 404 is firmly inserted into main unit of the $CO_2$ gas nozzle 403 via an O-ring 407, and is prevented from moving in its axial direction by a stopper. Furthermore, an upper end of the main unit of the $CO_2$ gas nozzle 403 is connected into a nut 420, and a thread part of the nut 420 is threaded via an O-ring 422 and a sleeve 421 to a joint 418 of a nozzle support portion. This joint 418 is fixed by a ball and plunger 419 to a support plate 408 mounted to the frame of the medium filling and harvesting apparatus, and this support plate 408 is interconnected with the lower valve case 410 by the support column 411. Still furthermore, an upper valve case 409 is firmly threaded via a screw or the like to an upper portion of the lower valve case 410 and chuck rubbers 412 opposing collars 415 connecting into the inner portions of both valve cases 409 and 410 are fixed and housed a fixing fitting 413 having small holes 413a. Medium is supplied from the medium supply member at the end of the silicon tube 423 that is fixed to the valve cases 409 and 410, passes through the gap 423a between the external wall of a mandrel 416 and the inner wall of the silicon tube 423, and is supplied into the inner nozzle 401 from the small holes 416b and the through holes 416a in the mandrel 416. The medium then passes through the strainer and is supplied to inside the roller bottles to fill them.

The opening part of the silicon tube 405 is connected to a $CO_2$ gas source and the supplied $CO_2$ gas first has its pH value measured, and if adjustment of the pH value is necessary, the $CO_2$ gas is sent via through holes 405a and 404a into the gap formed by the inner nozzle 401 and the outer nozzle 402, and is flushed almost simultaneously with the supply to the roller bottles of the medium from the end portion of the outer nozzle 402, and the pH value of the medium is adjusted. (Refer to the arrow B in FIG. 19.)

Moreover, adjusting the amount of medium is performed by the compressed air from the compressed air supply nipple 414 passing through the small holes 413a of the fixing fitting 413 into both or either the air chambers in the chuck rubbers 412, to expand the chuck rubbers 412 and deform the inner side of the silicon tube 423. As a result, the silicon tube 423 functions as a pinch valve so that the amount of medium in the small holes 416b and the through holes 416 and flowing to the inner nozzle 401 is controlled.

This embodiment of the nozzle for the simultaneous introduction of the culture medium and $CO_2$ has the configuration as described above and so when automatic and high-speed culture of adhesive animal cells is performed using roller bottles, the medium (culture liquid) inside the roller bottles is filled and its pH value can be adjusted with $CO_2$ gas almost simultaneously. Because of this, it is possible to achieve a significant increase in the processing performance of the roller bottle filling and harvesting system.

In addition, aeration of the medium is prevented and because there is a negative pressure inside the inner nozzle when the silicon tube is restored into the original state, drops do not occur from the end of the inner nozzle. Furthermore, it is possible to configure an unmanned system for the filling and harvesting of medium to and from roller bottles and so contamination due to microscopic organisms carried on the human body can be significantly reduced, a high and uniform productivity of the object subatances can be expected.

While the presently preferred embodiments of the present invention have been shown and described, it is to be understood that this disclosure is for the purpose of illustration and that various changes and modifications may be made without departing from the spirit and scope of the invention as set forth in the appended claims.

We claim:

1. A roller bottle filling and harvesting system wherein a decapper, a medium harvesting and cleaning apparatus, a medium filling apparatus and a capper are disposed in an aseptic chamber, comprising a medium harvesting and cleaning apparatus provided with a roller bottle feed that aligns the pitch of a plural number of roller bottles, simultaneously tilts said plural number of roller bottles from the upright position and to a predetermined angle and withdraws medium from said roller bottles, and returns said roller bottles to the upright position, a roller bottles inner surface cleaning apparatus to introduce cleaning liquid into said roller bottles, a roller bottle tilt and roll apparatus to tilt said roller bottles to a predetermined angle and rotate the same for a predetermined time and then transfer the same to a supply conveyor provided adjacently, and means for simultaneously tilting to a predetermined angle said plural number of roller bottles aligned and supplied from said medium filling apparatus, withdraw said cleaning liquid from the inside of said roller bottles, return said roller bottles to the upright position, introduce predetermined amounts of medium and $CO_2$ simultaneously into said roller bottles through a double nozzle, and transfer said roller bottles to a supply conveyor provided adjacently thereof, said roller bottle feeder further comprising:
 a plural number of bottle feed levers adapted to advance the roller bottles along a horizontal table of the apparatus, said feed levers being fixed to a tact rod that rises from and sinks at a predetermined cycle from slits in said horizontal table,
 a support bracket that axially supports support rollers supporting said tact rods so as to be freely reciprocating in the horizontal direction,
 a drive shaft fixed to a raising and lowering cam that causes said roller support brackets to rise and fall at a predetermined cycle,
 a rocking lever to produce a rocking motion in said bottle feed levers so that they reciprocate horizontally at a predetermined cycle, and
 a feed cam fixed to said drive shaft so that a rocking motion of a predetermined angle is transferred to said rocking lever.

2. The roller bottles filling and harvesting system according to claim 7, wherein said roller bottle inner surface cleaning apparatus comprises:
 a nozzle tip with a beveled member at an end portion thereof, and
 a strainer of fine metal mesh inserted between said bevelled portion and a nozzle sleeve end portion provided apart and in the direction of the axis of said nozzle tip.

3. The roller bottle filling and harvesting system according to claim 2 wherein said bevelled member is inclined upwards from the tip of said nozzle at an angle of between 20° and 80°.

4. The roller bottle filling and harvesting system according to claim 1 wherein said double nozzle comprises:
 an inner nozzle comprising a tube body,
 an outer nozzle comprising a second tube body coaxially provided on the outside of said inner nozzle so that a gap is formed, and
 a cylindrical strainer of fine metal mesh and having a bottom surface and inserted into an end portion of said inner nozzle, whereby medium is supplied via said inner nozzle and $CO_2$ gas is simultaneously supplied via said gap.

5. A roller bottle filling and harvesting system wherein a decapper, a medium harvesting and cleaning apparatus, a medium filling apparatus and a capper are disposed in an aseptic chamber, comprising a medium harvesting and cleaning apparatus provided with a roller bottle feeder that aligns the pitch of a plural number of roller bottles, simultaneously tilts said plural number of roller bottles from the upright position and to a predetermined angle and withdraws medium from said roller bottles, and returns said roller bottles to the upright position, a roller bottle inner surface cleaning apparatus to introduce cleaning liquid into said roller bottles, a roller bottle tilt and roll apparatus to tilt said roller bottles to a predetermined angle and rotate the same for a predetermined time and then transfer the same to a supply conveyor provided adjacently, and means for simultaneously tilting to a predetermined angle said plural number of roller bottles aligned and supplied from said medium filling apparatus, withdraw said cleaning liquid from the inside of said roller bottles, return said roller bottles to the upright position, introduce predetermined amounts of medium and $CO_2$ simultaneously into said roller bottles through a double nozzle, and transfer said roller bottles to a supply conveyor provided adjacently thereof, said roller bottle tilt and roll apparatus further comprising:
 a plural number of rubber rollers to rotate said roller bottles and fixed to a first roller shaft rotatably supported in a support plate,
 an inclined second shaft rotatably supported in a frame for tilting said support plate to a predetermined angle,
 a third drive shaft to transmit to said roller shaft the rotational motion of a drive motor interconnected with said drive shaft, and
 a vacuum pad and bottle holder fixed to said support plate and that attaches to said roller bottles and tilts the same.

6. The roller bottle filling and harvesting system according to claim 5, wherein said roller bottles inner surface cleaning apparatus further comprises:
 a nozzle tip with a bevelled member at an end portion thereof, and
 a strainer of fine metal mesh inserted between said bevelled portion and a nozzle sleeve end portion provided apart and in the direction of the axis of said nozzle tip.

7. The roller bottle filling and harvesting system according to claim 6, wherein said bevelled member is inclined upwards from the tip of said nozzle at an angle of between 20° and 80°.

8. The roller bottle filling and harvesting system according to claim 5 wherein said double nozzle comprises:

an inner nozzle comprising a tube body, an outer nozzle comprising a second tube body coaxially provided on the outside of said inner nozzle so that a gap is formed, and a cylindrical strainer of fine metal mesh and having a bottom surface and inserted into an end portion of said inner nozzle, whereby medium is supplied via said inner nozzle and $CO_2$ gas is simultaneously supplied via said gap.

* * * * *